United States Patent [19]
Kohl et al.

[11] Patent Number: 4,758,579
[45] Date of Patent: Jul. 19, 1988

[54] FLUOROALKOXY SUBSTITUTED BENZIMIDAZOLES USEFUL AS GASTRIC ACID SECRETION INHIBITORS

[75] Inventors: Bernhard Kohl; Ernst Sturm; Georg Rainer, all of Konstanz, Fed. Rep. of Germany

[73] Assignee: BYK Gulden Lomberg Chemische Fabrik GmbH, Konstanz, Fed. Rep. of Germany

[21] Appl. No.: 45,799

[22] Filed: Apr. 28, 1987

Related U.S. Application Data

[63] Continuation of Ser. No. 748,591, Jun. 14, 1985, abandoned.

[30] Foreign Application Priority Data

Jun. 16, 1984 [CH] Switzerland .................. 2899/84
Jun. 16, 1984 [CH] Switzerland .................. 2901/84

[51] Int. Cl.$^4$ .................. C07D 403/12; A61K 31/44
[52] U.S. Cl. .................. 514/338; 546/271
[58] Field of Search .................. 546/271; 514/338

[56] References Cited

U.S. PATENT DOCUMENTS

| | | |
|---|---|---|
| 4,255,431 | 3/1981 | Junggren .................. 546/271 |
| 4,337,257 | 6/1982 | Junggren .................. 546/271 |
| 4,435,406 | 3/1984 | Krassó .................. 546/271 |
| 4,472,409 | 9/1984 | Senn-Bilfinger .................. 546/271 |
| 4,508,905 | 4/1985 | Junggren .................. 546/271 |
| 4,555,518 | 11/1985 | Rainer .................. 546/271 |
| 4,560,693 | 12/1985 | Rainer .................. 546/271 |

FOREIGN PATENT DOCUMENTS 0004793 10/1979 European Pat. Off. .
0074341 3/1983 European Pat. Off. .
1234058 6/1971 United Kingdom .

OTHER PUBLICATIONS

Besso, *Chemical Abstracts*, vol. 86, p. 522, 188857n, 1977.
Besso, *Bulletin of the Chemical Society of Japan*, vol. 50(3), 710–712, 1977.
Imafuku, *Chemical Abstracts*, vol. 90, p. 534, 167745s, 1979.
Brown, *Chemical Abstracts*, vol. 92, p. 596, 94426t, 1980.

*Primary Examiner*—Jane T. Fan
*Attorney, Agent, or Firm*—Berman, Aisenberg & Platt

[57] ABSTRACT

Dialkoxypyridines of formula I

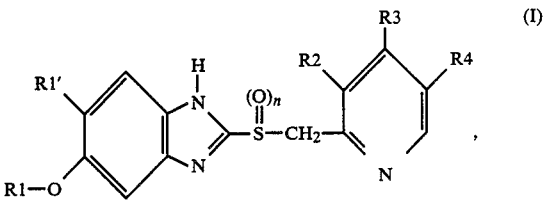

wherein
R1 is 1–3C-alkyl which is completely or predominantly substituted by fluorine, or a chlorodifluoromethyl radical and
R1' is hydrogen, halo, trifluoromethyl, 1–3C-alkyl, or 1–3C-alkoxy which is optionally completely or predominantly substituted by fluorine, or
R1 and R1', together with the oxygen atom to which R1 is bonded, are 1–2C-alkylenedioxy, which is optionally completely or partly substituted by fluorine, or chlorotrifluoroethylenedioxy,
R3 is 1–3C-alkoxy,
one of R2 and R4 is 1–3C-alkoxy and the other is a hydrogen atom or 1–3C-alkyl and
n is 0 or 1, and salts thereof are new compounds with a pronounced protective action on the stomach. Processes for preparing these compounds, medicaments containing them and their use, as well as intermediate compounds and their use for preparing the subject dialkoxypyridines, are disclosed.

28 Claims, No Drawings

FLUOROALKOXY SUBSTITUTED BENZIMIDAZOLES USEFUL AS GASTRIC ACID SECRETION INHIBITORS

This application is a continuation of Ser. No. 748,591, filed June 14, 1985 now abandoned.

RELATED APPLICATIONS

The disclosed and claimed subject matter is related to that of applications Ser. No. 606,872 (filed May 1, 1984), Ser. No. 606,873 (filed May 1, 1984) and Ser. No. 794,230 (filed Oct. 29, 1985) now abandoned.

FIELD OF THE INVENTION

The invention relates to new dialkoxypyridines, processes for their preparation, their use and medicaments containing them. The compounds according to the invention are used in the pharmaceutical industry as intermediates and for the preparation of medicaments.

BACKGROUND

European Patent Application No. 0,005,129 concerns substituted pyridylsulfinylbenzimidazoles which are said to have properties of inhibiting secretion of gastric acid. The use of a number of benzimidazole derivatives for inhibiting secretion of gastric acid is referred to in European Patent Application No. 0,074,341. British Patent Application GB No. 2,082,580 involves tricyclic imidazole derivatives which are said to inhibit secretion of gastric acid and to prevent ulcer formation. In U.S. Pat. No. 4,472,409 and in U.S. applications Ser. No. 606,872 and Ser. No. 606,873 (both filed on May 1, 1984) trifluoromethyl compounds, fluoroalkoxy compounds and tricyclic ethers with benzimidazole structure and a marked protective effect on the stomach are described.

SUMMARY OF THE INVENTION

It has now been found, surprisingly, that the dialkoxypyridines of the present invention have interesting and unexpected properties which advantageously distinguish them from known compounds.

The invention relates to dialkoxypyridines of formula I and salts thereof, to medicament compositions having (as an active ingredient thereof) an effective amount of a compound of formula I or of a pharmaceutically-acceptable salt thereof, to the use of these compounds and compositions to inhibit gastric acid secretion in and to protect the stomach and intestines of warm-blooded animals, to the formulation of the medicament compositions, to the synthesis of dialkoxypyridines of formula I and of salts thereof, to compounds of formula III and to their use in preparing compounds of formula I and salts of the latter.

An object of this invention is to provide compounds and compositions useful for inhibiting gastric acid secretion in warm-blooded animals.

Another object is to provide compounds and compositions which protect the stomach and intestines of warm-blooded animals.

A further object is to provide chemically-stable compounds and compositions which have a wide therapeutic range and lack substantial side effects and especially to impart higher chemical stability to pyridylsulfinyl-benzimidazoles.

Still further objects are apparent from the following description.

DETAILS

The invention relates to new dialkoxypyridines of formula I:

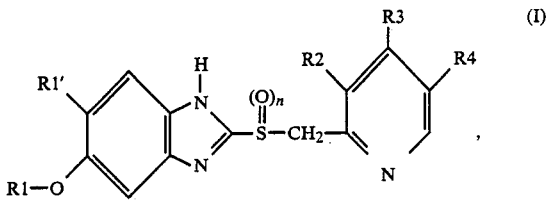

wherein
R1 represents a 1–3C-alkyl radical which is completely or predominantly substituted by fluorine, or a chlorodifluoromethyl radical and
R1' represents hydrogen (—H), halo, trifluoromethyl, a 1–3C-alkyl radical, or a 1–3C-alkoxy radical which is, optionally, completely or predominantly substituted by fluorine, or
R1 and R1' together, with inclusion of the oxygen atom to which R1 is bonded, represent a 1–2C-alkylenedioxy radical which is, optionally, completely or partly substituted by fluorine, or a chlorotrifluoroethylenedioxy radical,
R3 represents a 1–3C-alkoxy radical,
one of the radicals R2 and R4 represents a 1–3C-alkoxy radical and the other represents a hydrogen atom (—H) or a 1–3C-alkyl radical and
n represents the number 0 or 1,
and to salts of these compounds.

Examples of 1–3C-alkyl radicals which are completely or predominantly substituted by fluorine are the 1,1,2-trifluoroethyl radical, the perfluoropropyl radical, the perfluoroethyl radical, and in particular, the 1,1,2,2-tetrafluoroethyl radical, the trifluoromethyl radical, the 2,2,2-trifluoroethyl radical and the difluoromethyl radical.

Halogen in the context of the present invention is bromine, chlorine and, in particular, fluorine.

1–3C-alkyl radicals are the propyl, isopropyl, ethyl and, in particular, methyl radical.

1–3C-alkoxy radicals contain, in addition to the oxygen atom, the mentioned 1–3C-alkyl radicals. The methoxy radical is preferred.

1–3C-Alkoxy radicals which are completely or predominantly substituted by fluorine contain, in addition to the oxygen atom, the mentioned 1–3C-alkyl radicals which are completely or predominantly substituted by fluorine. Examples include the 1,1,2,2-tetrafluoroethoxy, the trifluoromethoxy, the 2,2,2-trifluoroethoxy and the difluoromethoxy radicals.

Examples of 1–2C-alkylenedioxy radicals which are, optionally, completely or partly substituted by fluorine are the 1,1-difluoroethylenedioxy radical (—O—CF$_2$—CH$_2$—O—), the 1,1,2,2L-tetrafluoroethylenedioxy radical (—O—CF$_2$—CF$_2$—O—), the 1,1,2-trifluoroethylenedioxy radical (—O—CF$_2$—CHF—O—) and, in particular, the difluoromethylenedioxy radical (—O—CF$_2$—O—), as substituted radicals, and the ethylenedioxy radical and the methylenedioxy radical, as unsubstituted radicals.

Preferred salts of compounds of the formula I in which n denotes the number 0 (sulfides) are all the acid-addition salts. The pharmacologically-acceptable salts of inorganic and organic acids usually employed in galenics are notable examples. Pharmacologically-unacceptable salts which may be obtained initially via industrial-scale processes are converted into pharmacologically-acceptable salts by conventional processes. Examples of suitable pharmacologically-acceptable salts are water-soluble and water-insoluble acid-addition salts, such as the hydrochloride, hydrobromide, hydriodide, phosphate, nitrate, sulfate, acetate, citrate, gluconate, benzoate, hibenzate, fendizoate, butyrate, sulfosalicylate, maleate, laurate, malate, fumarate, succinate, oxalate, tartrate, amsonate, embonate, metembonate, stearate, tosylate, 2-hydroxy-3-naphthoate, 3-hydroxy-2-naphthoate and mesylate.

Preferred salts of compounds of formula I in which n denotes 1 (sulfoxides) are basic salts, in particular pharmacologically-acceptable salts with inorganic and organic bases usually employed in pharmacy. Examples of pharmacologically-acceptable basic salts are the sodium, potassium, calcium and aluminum salts.

One embodiment (embodiment a) of the invention comprises compounds of formula I wherein R1' represents hydrogen (—H), and R1, R2, R3, R4 and n have the previously-noted meanings; and their salts.

Another embodiment (embodiment b) of the invention comprises compounds of formula I wherein R1' represents halogen, trifluoromethyl, a 1-3C-alkyl radical or a 1-3C-alkoxy radical which is, optionally, completely or predominantly substituted by fluorine; and R1, R2, R3, R4 and n have the previously-mentioned meanings; and their salts.

Another embodiment (embodiment c) of the invention comprises compounds of formula I wherein R1 and R1' together, including the oxygen atom to which R1 is bonded, comprise a 1-2C-alkylenedioxy radical, and R2, R3, R4 and n have the aforementioned meanings; and their salts.

Another embodiment (embodiment d) of the invention comprises compounds of formula I wherein R1 and R1' together, including the oxygen atom to which R1 is bonded, comprise a 1-2C-alkylenedioxyradical which is completely or partly substituted by fluorine, and R2, R3, R4 and n have the previously-noted meanings; and their salts.

Another embodiment (embodiment e) of the invention comprises compounds of formula I wherein R1 and R1' together, including the oxygen atom to which R1 is bonded, comprise a chlorotrifluoroethylenedioxy radical, and R2, R3, R4 and n have their previously-ascribed meanings; and their salts.

Preferred compounds of embodiment a are those of formula I wherein R1 represents 1,1,2,2-tetrafluoroethyl, trifluoromethyl, 2,2,2-trifluoroethyl, difluoromethyl or chlorodifluoromethyl, R1' represents hydrogen, R3 represents methoxy, one of the radicals R2 and R4 represents methoxy and the other represents hydrogen or methyl, and n represents the number 0 or 1; and the salts of these compounds.

Preferred compounds of embodiment b are those of formula I wherein R1 represents difluoromethyl, R1' represents difluoromethoxy or methoxy, R3 represents methoxy, one of the radicals R2 and R4 represent methoxy and the other represents hydrogen or methyl, and n represents the number 0 or 1; and the salts of these compounds.

Preferred compounds of embodiment c are those of formula I wherein R1 and R1' together, combined with the oxygen atom to which R1 is bonded, represent a methylenedioxy or ethylenedioxy radical, R3 represents methoxy, one of the radicals R2 and R4 represents methoxy and the other represents hydrogen or methyl, and n represents the number 0 or 1; and the salts of these compounds.

Preferred compounds of embodiment d are those of formula I wherein R1 and R1' together, combined with the oxygen atom to which R1 is bonded, represent a difluoromethylenedioxy radical or a 1,1,2-trifluoroethylenedioxy radical, R3 represents methoxy, one of the radicals R2 and R4 represents methoxy and the other represents hydrogen or methyl, and n represents the number 0 or 1; and the salts of these compounds.

Preferred compounds of embodiment e are those of formula I wherein R1 and R1' together, including the oxygen atom to which R1 is bonded, represent a chlorotrifluoroethylenedioxy radical, R3 represents methoxy, one of the radicals R2 and R4 represents methoxy and the other represents hydrogen or methyl, and n represents 0 or 1; and the salts of these compounds.

Examples of compounds according to the invention are:

2-[(4,5-dimethoxy-3-methyl-2-pyridyl)methylsulfinyl]-5-trifluoromethoxy-1H-benzimidazole, 2-[(4,5-dimethoxy-3-methyl-2-pyridyl)-methylthio]-5-trifluoromethoxy-1H-benzimidazole, 2-[(4,5-dimethoxy-3-methyl-2-pyridyl)methylsulfinyl]-5-(1,1,2,2-tetrafluoroethoxy)-1H-benzimidazole, 2-[(4,5-dimethoxy-3-methyl-2-pyridyl)methylthio]-5-(1,1,2,2-tetrafluoroethoxy)-1H-benzimidazole, 2-[(4,5-dimethoxy-3-methyl-2-pyridyl)methylsulfinyl]-5-(2,2,2-trifluoroethoxy)-1H-benzimidazole, 2-[(4,5-dimethoxy-3-methyl-2-pyridyl)-methylthio]-5-(2,2,2-trifluoroethoxy)-1H-benzimidazole, 5-difluoromethoxy-2-[(4,5-dimethoxy-3-methyl-2-pyridyl)methylsulfinyl]-1H-benzimidazole, 5-difluoromethoxy-2-[(4,5-dimethoxy-3-methyl-2-pyridyl)methylthio]-1H-benzimidazole, 5-chlorodifluoromethoxy-2-[(4,5-dimethoxy-3-methyl-2-pyridyl)methylsulfinyl]-1H-benzimidazole, 5-chlorodifluoromethoxy-2-[(4,5-dimethoxy-3-methyl-2-pyridyl)methylthio]-1H-benzimidazole, 5,6-bis(difluoromethoxy)-2-[(4,5-dimethoxy-3-methyl-2-pyridyl)methylsulfinyl]-1H-benzimidazole, 5,6-bis(difluoromethoxy)-2-[(4,5-dimethoxy-3-methyl-2-pyridyl)methylthio]-1H-benzimidazole, 5-difluoromethoxy-6-methoxy-2-[(4,5-dimethoxy-3-methyl-2-pyridyl)methylsulfinyl]-1H-benzimidazole, 5-difluoromethoxy-6-methoxy-2-[(4,5-dimethoxy-3-methyl-2-pyridyl)-methylthio]-1H-benzimidazole, 2-[(4,5-dimethoxy-2-pyridyl)methylsulfinyl]-5-trifluoromethoxy-1H-benzimidazole, 2-[(4,5-dimethoxy-2-pyridyl)methylthio]-5-trifluoromethoxy-1H-benzimidazole, 2-[(4,5-dimethoxy-2-pyridyl)methylsulfinyl]-5-(1,1,2,2-tetrafluoroethoxy)-1H-benzimidazole, 2-[(4,5-dimethoxy-2-pyridyl)methylthio]-5-(1,1,2,2-tetrafluoroethoxy)-1H-benzimidazole, 2-[(4,5-dimethoxy-2-pyridyl)methylsulfinyl]-5-(2,2,2-trifluoroethoxy)-1H-benzimidazole, 2-[(4,5-dimethoxy-2-pyridyl)methylthio]-5-(2,2,2-trifluoroethoxy)-1H-benzimidazole, 5-difluoromethoxy-2-[(4,5-dimethoxy-2-pyridyl)methylsulfinyl]-1H-benzimidazole, 5-difluoromethoxy-2-[(4,5-dimethoxy-2-pyridyl)methylthio]-1H-benzimidazole, 5-chlorodifluoromethoxy-2-[(4,5-dimethoxy-2-pyridyl)methylsulfinyl]-1H-benzimidazole, 5-chlorodifluoromethoxy-2-[(4,5-dimethoxy-2-pyridyl)-methylthio]-1H-benzimidazole,
5,6-bis(difluoromethoxy)-2-[(4,5-dimethoxy-2-pyridyl)-methylsulfinyl]-1H-benzimidazole,
5,6-bis(difluoromethoxy)-2-[(4,5-dimethoxy-2-pyridyl)-methylthio]-1H-benzimidazole,
5-difluoromethoxy-6-methoxy-2-[(4,5-dimethoxy-2-pyridyl)methylsulfinyl]-1H-benzimidazole,
5-difluoromethoxy-6-methoxy-2-[4,5-dimethoxy-2-pyridyl)methylthio]-1H-benzimidazole,
2-[(3,4-dimethoxy-5-methyl-2-pyridyl)methylsulfinyl]-5-trifluoromethoxy-1H-benzimidazole,
2-[(3,4-dimethoxy-5-methyl-2-pyridyl)methylthio]-5-trifluoromethoxy-1H-benzimidazole,
2,[(3,4-dimethoxy-5-methyl-2-pyridyl)methylsulfinyl]-5-(1,1,2,2-tetrafluoroethoxy)-1H-benzimidazole,
2-[(3,4-dimethoxy-5-methyl-2-pyridyl)methylthio]-5-(1,1,2,2-tetrafluoro-ethoxy)-1H-benzimidazole,
2-[(3,4-dimethoxy-5-methyl-2-pyridyl)methylsulfinyl]-5-(2,2,2-trifluoroethoxy)-1H-benzimidazole,
2-[(3,4-dimethoxy-5-methyl-2-pyridyl)-methylthio]-5-(2,2,2-trifluoroethoxy)-1H-benzimidazole,
5-difluoromethoxy-2-[(3,4-dimethoxy-5-methyl-2-pyridyl)methylsulfinyl]-1H-benzimidazole,
5-difluoromethoxy-2-[(3,4-dimethoxy-5-methyl-2-pyridyl)methylthio]-1H-benzimidazole,
5-chlorodifluoromethoxy-2-[(3,4-dimethoxy-5-methyl-2-pyridyl)methylsulfinyl]-1H-benzimidazole,
5-chlorodifluoromethoxy-2-[(3,4-dimethoxy-5-methyl-2-pyridyl)methylthio]-1H-benzimidazole,
5,6-bis(difluoromethoxy)-2-[(3,4-dimethoxy-5-methyl-2-pyridyl)methylsulfinyl]-1H-benzimidazole,
5,6-bis(difluoromethoxy)-2-[(3,4-dimethoxy-5-methyl-2-pyridyl)methylthio]-1H-benzimidazole,
5-difluoromethoxy-6-methoxy-2-[(3,4-dimethoxy-5-methyl-2-pyridyl)methylsulfinyl]-1H-benzimidazole,
5-difluoromethoxy-6-methoxy-2-[(3,4-dimethoxy-5-methyl-2-pyridyl)methylthio]-1H-benzimidazole,
2-[(3,4-dimethoxy-2-pyridyl)methylsulfinyl]-5-trifluoromethoxy-1H-benzimidazole,
2-[(3,4-dimethoxy-2-pyridyl)methylthio]-5-trifluoromethoxy-1H-benzimidazole,
2-[(3,4-dimethoxy-2-pyridyl)methylsulfinyl]-5-(1,1,2,2-tetrafluoroethoxy)-1H-benzimidazole,
2-[(3,4-dimethoxy-2-pyridyl)methylthio]-5-(1,1,2,2-tetrafluoroethoxy)-1H-benzimidazole,
2-[(3,4-dimethoxy-2-pyridyl)methylsulfinyl]-5-(2,2,2-trifluoroethoxy)-1H-benzimidazole,
2-[(3,4-dimethoxy-2-pyridyl)methylthio]-5-(2,2,2-trifluoroethoxy)-1H-benzimidazole,
5-difluoromethoxy-2-[(3,4-dimethoxy-2-pyridyl)methylsulfinyl]-1H-benzimidazole,
5-difluoromethoxy-2-[(3,4-dimethoxy-2-pyridyl)methylthio]-1H-benzimidazole,
5-chlorodifluoromethoxy-2-[(3,4-dimethoxy-2-pyridyl)-methylsulfinyl]-1H-benzimidazole,
5-chlorodifluoromethoxy-2-[(3,4-dimethoxy-2-pyridyl)methylthio]-1H-benzimidazole,
5,6-bis(difluoromethoxy)-2-[(3,4-dimethoxy-2-pyridyl)methylsulfinyl]-1H-benzimidazole,
5,6-bis(difluoromethoxy)-2-[(3,4-dimethoxy-2-pyridyl)methylthio]-1H-benzimidazole,
5-difluoromethoxy-6-methoxy-2-[(3,4-dimethoxy-2-pyridyl)methylsulfinyl]-1H-benzimidazole,
5-difluoromethoxy-6-methoxy-2-[(3,4-dimethoxy-2-pyridyl)methylthio]-1H-benzimidazole,
2,2-difluoro-6-[(4,5-dimethoxy-2-pyridyl)methylsulfinyl]-5H-[1,3]-dioxolo-[4,5-f]benzimidazole,
2,2-difluoro-6-[(4,5-dimethoxy-2-pyridyl)methylthio]-5H-[1,3]-dioxolo-[4,5-f]benzimidazole,
2,2-difluoro-6-[(3-methyl-4,5-dimethoxy-2-pyridyl)methylthio]-5H-[1,3]-dioxolo[4,5-f]benzimidazole,
2,2-difluoro-6-[(3-methyl-4,5-dimethoxy-2-pyridyl)methylsulfinyl]-5H-[1,3]-dioxolo[4,5-f]benzimidazole,
6-[(4,5-diethoxy-3-methyl-2-pyridyl)methylthio]-2,2-difluoro-5H-[1,3]-dioxolo[4,5-f]benzimidazole,
6-[(4,5-diethoxy-3-methyl-2-pyridyl)methylsulfinyl]-2,2-difluoro-5H-[1,3]-dioxolo[4,5-f]benzimidazole,
6,6,7-trifluoro-6,7-dihydro-2-[(4,5-dimethoxy-3-methyl-2-pyridyl)methylthio-1H-[1,4]-dioxino[2,3-f]benzimidazole,
6,6,7-trifluoro-6,7-dihydro-2-[(4,5-dimethoxy-3-methyl-2-pyridyl)methylsulfinyl]-1H-[1,4]-dioxino[2,3-f]benzimidazole,
6,6,7-trifluoro-6,7-dihydro-2-[(4,5-dimethoxy-2-pyridyl)methylthio]-1H-[1,4]-dioxino-[2,3-f]benzimidazole,
6,6,7-trifluoro-6,7-dihydro-2-[(4,5-dimethoxy-2-pyridyl)methylsulfinyl]-1H-[1,4]-dioxino[2,3-f]benzimidazole,
2-[(4,5-diethoxy-2-pyridyl)methylthio]6,6,7-trifluoro-6,7-dihydro-1H-[1,4]-dioxino[2,3-f]benzimidazole,
2-[(4,5-diethoxy-2-pyridyl)methylsulfinyl]-6,6,7-trifluoro-6,7-dihydro-1H-[1,4]-dioxino[2,3-f]benzimidazole,
2-[(4,5-diethoxy-3-methyl-2-pyridyl)methylthio]-6,6,7-trifluoro-6,7-dihydro-1H-[1,4]-dioxino[2,3-f]benzimidazole,
2-[(4,5-diethoxy-3-methyl-2-pyridyl)methylsulfinyl]-6,6,7-trifluoro-6,7-dihydro-1H-[1,4]-dioxino[2,3-f]benzimidazole,
6,6-difluoro-6,7-dihydro-2-[(4,5-dimethoxy-2-pyridyl)-methylthio]-1H-[1,4]-dioxino[2,3-f]benzimidazole,
6,6-difluoro-6,7-dihydro-2-[(4,5-dimethoxy-2-pyridyl)-methylsulfinyl]-1H-[1,4]-dioxinio[2,3-f]benzimidazole,
6,6-difluoro-6,7-dihydro-2-[(4,5-dimethoxy-3-methyl-2-pyridyl)methylthio]-1H-[1,4]-dioxino[2,3-f]benzimidazole,
6,6-difluoro-6,7-dihydro-2-[(4,5-dimethoxy-3-methyl-2-pyridyl)methylsulfinyl]-1H-[1,4]-dioxino[2,3-f]benzimidazole,
6,6,7,7-tetrafluoro-6,7-dihydro-2-[(4,5-dimethoxy-2-pyridyl)methylthio]-1H-[1,4]-dioxino[2,3-f]benzimidazole,
6,6,7,7-tetrafluoro-6,7-dihydro-2-[(4,5-dimethoxy-2-pyridyl)methylsulfinyl]-1H-[1,4]-dioxino[2,3-f]benzimidazole,
6,6,7,7-tetrafluoro-6,7-dihydro-2-[(4,5-dimethoxy-3-methyl-2-pyridyl)methylthio]-1H-[1,4]-dioxino[2,3-f]benzimidazole,
6,6,7,7-tetrafluoro-6,7-dihydro-2-[(4,5-dimethoxy-3-methyl-2-pyridyl)methylsulfinyl]-1H-[1,4]-dioxine[2,3-f]benzimidazole,
6-chloro-6,7,7-trifluoro-6,7-dihydro-2-[(4,5-dimethoxy-3-methyl-2-pyridyl)methylsulfinyl]-1H-[1,4]dioxino[2,3-f]benzimidazole,
6-chloro-6,7,7-trifluoro-6,7-dihydro-2-[(4,5-dimethoxy-3-methyl-2-pyridyl)methylthio]-1H-[1,4]-dioxino[2,3-f]benzimidazole,
6-chloro-6,7,7-trifluoro-6,7-dihydro-2-[(4,5-dimethoxy-2-pyridyl)methylsulfinyl]-1H-[1,4]-dioxino[2,3-f]-benzimidazole,
6-chloro-6,7,7-trifluoro-6,7-dihydro-2-[(4,5-dimethoxy-2-pyridyl)methylthio]-1H-[1,4]-dioxino[2,3-f]benzimidazole, 2,2-difluoro-6-[(3,4-dimethoxy-2-pyridyl)methylsulfinyl]-5H-[1,3]-dioxolo[4,5-f]benzimidazole,
2,2-difluoro-6-[(3,4-dimethoxy-2-pyridyl)methylthio]-5H-[1,3]-dioxolo-[4,5-f]benzimidazole,
2,2-difluoro-6-[(3,4-dimethoxy-5-methyl-2-pyridyl)methylthio]-5H-[1,3]-dioxolo[4,5-f]benzimidazole,
2,2-difluoro-6-[(3,4-dimethoxy-5-methyl-2-pyridyl)methylsulfinyl]-5H-[1,3]-dioxolo[4,5-f]benzimidazole,
6-[(3,4-diethoxy-5-methyl-2-pyridyl)methylthio]-2,2-difluoro-5H-[1,3]-dioxolo[4,5-f]benzimidazole,
6-[(3,4-diethoxy-5-methyl-2-pyridyl)methylsulfinyl]-2,2-difluoro-5H-[1,3]-dioxolo[4,5-f]benzimidazole,
6,6,7-trifluoro-6,7-dihydro-2-[(3,4-dimethoxy-5-methyl-2-pyridyl)methylthio]-1H-[1,4]-dioxino[2,3-f]benzimidazole,
6,6,7-trifluoro-6,7-dihydro-2-[(3,4-dimethoxy-5-methyl-2-pyridyl)methylsulfinyl]-1H-[1,4]-dioxino[2,3-f]benzimidazole,
6,6,7-trifluoro-6,7-dihydro-2-[(3,4-dimethoxy-2-pyridyl)methylthio]-1H-[1,4]-dioxino[2,3-f]benzimidazole,
6,6,7-trifluoro-6,7-dihydro-2-[(3,4-dimethoxy-2-pyridyl)methylsulfinyl]-1H-[1,4]-dioxino[2,3-f]benzimidazole,
2-[(3,4-diethoxy-2-pyridyl)methylthio]-6,6,7-trifluoro-6,7-dihydro-1H-[1,4]-dioxino[2,3-f]benzimidazole,
2-[(3,4-diethoxy-2-pyridyl)methylsulfinyl]-6,6,7-trifluoro-6,7-dihydro-1H-[1,4]-dioxino[2,3-f]benzimidazole,
2-[(3,4-diethoxy-5-methyl-2-pyridyl)methylthio]-6,6,7-trifluoro-6,7-dihydro-1H-[1,4]-dioxino[2,3-f]benzimidazole,
2-[(3,4-diethoxy-5-methyl-2-pyridyl)methylsulfinyl]-6,6,7-trifluoro-6,7-dihydro-1H-[1,4]-dioxino[2,3-f]benzimidazole,
6,6-difluoro-6,7-dihydro-2-[(3,4-dimethoxy-2-pyridyl)methylthio]-1H-[1,4]-dioxino[2,3-f]benzimidazole,
6,6-difluoro-6,7-dihydro-2-[(3,4-dimethoxy-2-pyridyl)methylsulfinyl]-1H-[1,4]-dioxino[2,3-f]benzimidazole,
6,6-difluoro-6,7-dihydro-2-[(3,4-dimethoxy-5-methyl-2-pyridyl)methylthio]-1H-[1,4]-dioxino[2,3-f]benzimidazole,
6,6-difluoro-6,7-dihydro-2-[(3,4-dimethoxy-5-methyl-2-pyridyl)methylsulfinyl]-1H-[1,4]-dioxino[2,3-f]benzimidazole,
6,6,7,7-tetrafluoro-6,7-dihydro-2-[(3,4-dimethoxy-2-pyridyl)methylthio]-1H-[1,4]-dioxino[2,3-f]benzimidazole,
6,6,7,7-tetrafluoro-6,7-dihydro-2-[(3,4-dimethoxy-2-pyridyl)methylsulfinyl]-1H-[1,4]-dioxino[2,3-f]benzimidazole,
6,6,7,7-tetrafluoro-6,7-dihydro-2-[(3,4-dimethoxy-5-methyl-2-pyridyl)methylthio]-1H-[1,4]-dioxino[2,3-f]benzimidazole,
6,6,7,7-tetrafluoro-6,7-dihydro-2-[(3,4-dimethoxy-5-methyl-2-pyridyl)methylsulfinyl]-1H-[1,4]-dioxino[2,3-f]benzimidazole,
6-chloro-6,7,7-trifluoro-6,7-dihydro-2-[(3,4-dimethoxy-5-methyl-2-pyridyl)methylsulfinyl]-1H-[1,4]-dioxino[2,3-f]benimidazole,
6-chloro-6,7,7-trifluoro-6,7-dihydro-2-[(3,4-dimethoxy-5-methyl-2-pyridyl)methylthio]-1H-[1,4]-dioxino[2,3-f]benzimidazole,
6-chloro-6,7,7-trifluoro-6,7-dihydro-2-[(3,4-dimethoxy-2-pyridyl)methylsulfinyl]-1H-[1,4]-dioxino[2,3-f]benzimidazole,
6-chloro-6,7,7-trifluoro-6,7-dihydro-2-[(3,4-dimethoxy-2-pyridyl)methylthio]-1H-[1,4]-dioxino[2,3-f]benzimidazole,
6-[(4,5-dimethoxy-3-methyl-2-pyridyl)-methylthio]-5H-[1,3]dioxolo[4,5-f]benzimidazole,
6-[(4,5-dimethoxy-3-methyl-2-pyridyl)-methylsulfinyl]-5H-[1,3]-dioxolo[4,5-f]benzimidazole,
6-[(4,5-dimethoxy-2-pyridyl)methylthio]-5H-[1,3]dioxolo[4,5-d]benzimidazole,
6-[(4,5-dimethoxy-2-pyridyl)methylsulfinyl]-5H-[1,3]-dioxolo[4,5-f]benzimidazole,
6-[(3,4-dimethoxy-2-pyridyl)-methylthio]-5H-[1,3]-dioxolo[4,5-f]benzimidazole,
6-[(3,4-dimethoxy-2-pyridyl)methylsulfinyl]-5H-[1,3]-dioxolo[4,5-f]benzimidazole.
6-[(3,4-dimethoxy-5-methyl-2-pyridyl)methylthio]-5H-[1,3]-dioxolo[4,5-f]-benzimidazole,
6-[(3,4-dimethoxy-5-methyl-2-pyridyl)methylsulfinyl]-5H-[1,3]-dioxolo[4,5-f]benzimidazole,
6,7-dihydro-2-[(4,5-dimethoxy-3-methyl-2-pyridyl)methylthio]-1H-[1,4]-dioxino[2,3-f]benzimidazole,
6,7-dihydro-2-[(4,5-dimethoxy-3-methyl-2-pyridyl)methylsulfinyl]-1H-[1,4]-dioxino[2,3-f]benzimidazole,
6,7-dihydro-2-[(3,4-dimethoxy-5-methyl-2-pyridyl)methylthio]-1H-[1,4]-dioxino[2,3-f]benzimidazole,
6,7-dihydro-2-[(3,4-dimethoxy-5-methyl-2-pyridyl)methylsulfinyl]-1H-[1,4]-dioxino[2,3-f]benzimidazole,
6,7-dihydro-2-[(3,4-dimethoxy-2-pyridyl)methylthio]-1H-[1,4]-dioxino[2,3-f]benzimidazole and
6,7-dihydro-2-[(4,5-dimethoxy-2-pyridyl)methylsulfinyl]-1H-[1,4]-dioxino[2,3-f]benzimidazole,
and salts of these compounds.

Due to the tautomerism in the imidazole ring, 5-substitution in the benzimidazole is identical to 6-substitution. Accordingly, in the compounds in which R1 and R1' together, with inclusion of the oxygen atom to which R1 is bonded, represent a substituted ethylenedioxy radical, the 6-position in the [1,4]-dioxino[2,3-f]benzimidazole part is identical to the 7-position.

The invention furthermore relates to a process for the preparation of the dialkoxypyridines of formula I, wherein R1, R1', R2, R3, R4 and n have their noted meanings, and of their salts.

The process comprises reacting:

(a) a mercaptobenzimidazole of formula II with a picoline derivative III

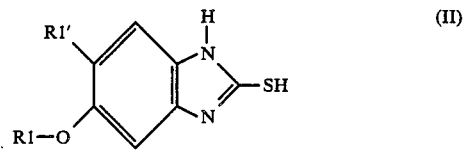 (II)

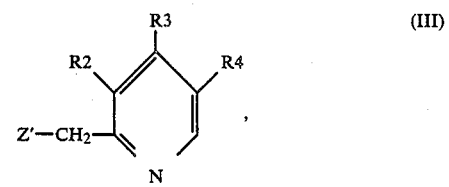 (III)

(b) a benzimidazole of formula IV with a mercaptopicoline V

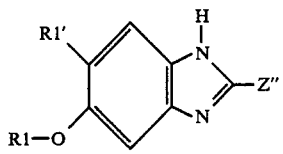  (IV)

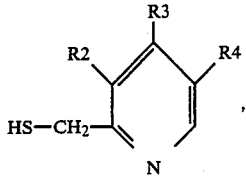  (V)

(c) an o-phenylenediamine of formula VI with a formic acid derivative VII

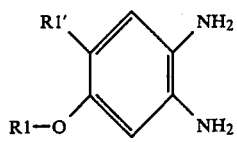  (VI)

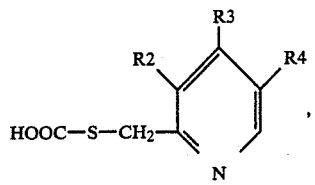  (VII)

and, if appropriate, the 2-benzimidazolyl 2-pyridylmethyl sulfides of formula VIII obtained according to (a), (b) or (c)

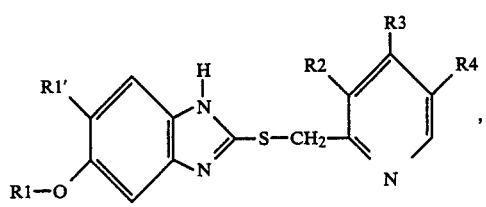  (VIII)

are then oxidized and/or converted into salts, (d) a benzimidazole of formula IX with a pyridine derivative X

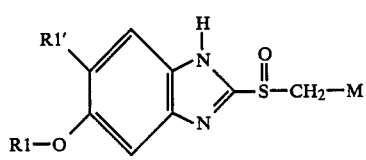  (IX)

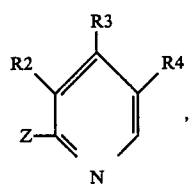  (X)

(e) a sulfinyl compound of formula XI with a 2-picoline derivative XII

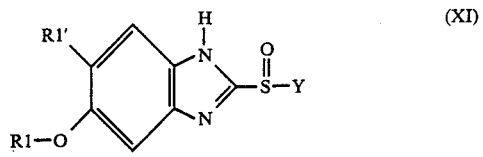  (XI)

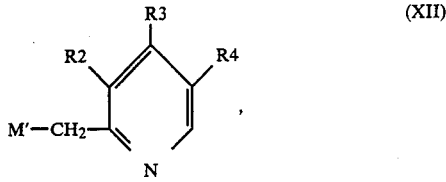  (XII)

and, if appropriate, the products are converted into salts, Y, Z, Z' and Z" being suitable leaving groups, M representing an alkali-metal atom (Li, Na or K), M' representing the equivalent of a metal atom and R1, R1', R2, R3, R4 and n having their above-mentioned meanings.

The compounds II–XII are employed in the indicated reactions in their free states or as salts.

Preparation processes (a), (b) and (c) lead to the sulfides according to the invention, and the oxidation of compounds VIII and processes (d) and (e) give sulfoxides according to the invention.

Those skilled in the art are familiar with suitable leaving groups Y, Z, Z' and Z". A suitable leaving group Y is, for example, a group which forms a reactive sulfinic acid derivative together with the sulfinyl group to which it is bonded. Examples of suitable leaving groups Y are alkoxy, dialkylamino and alkylmercapto groups. Examples of suitable leaving groups Z, Z' or Z" are halogen atoms, in particular chlorine atoms, or hydroxyl groups activated by esterification (for example with p-toluenesulfonic acid). The equivalent of a metal atom M' is, for example, an alkali-metal atom (Li, Na or K), or an alkaline-earth-metal atom (for example Mg), which is substituted by a halogen atom (for example Br, Grignard reagent), or any other optionally-substituted metal atom which is known to react like the noted metals in replacement reactions of organometallic compounds.

The reaction of II with III is carried out in known manner in suitable, preferably polar, protic or aprotic solvent (such as methanol, isopropanol, dimethyl sulfoxide, acetone, dimethylformamide or acetonitrile) with the addition of or exclusion of water. It is carried out, for example, in the presence of a proton acceptor. Examples of suitable proton acceptors are alkali-metal hydroxides, such as sodium hydroxide, alkali-metal carbonates, such as potassium carbonate, or tertiary amines, such as pyridine, triethylamine or ethyldiisopropylamine. Alternatively, the reaction is carried out without a proton acceptor, in which case, depending on the starting compounds, the acid-addition salts are first obtained in a particularly pure form. The reaction temperature is, e.g., between 0° and 150° C. (depending on the reactants involved), temperatures between 20° and 80° C. being preferred in the presence of proton acceptors and temperatures between 60° and 120° C. (in particular the boiling point of the solvent used) being preferred without proton acceptors. The reaction times are between 0.5 and 24 hours.

Reaction conditions similar to those in the reaction of II with III are used in the reaction of IV with V, which is carried out in a known manner.

The reaction of VI with VII is preferably carried out in polar, optionally water-containing solvents in the presence of a strong acid, for example hydrochloric acid, preferably at the boiling point of the solvent used.

The oxidation of the sulfides VIII is conventionally carried out under conditions known to be suitable for the oxidation of sulfides to sulfoxides [cf. J. Drabowicz and M. Mikolajczyk, *Organic Preparations and Procedures Int.* 14(1-2), 45-89 (1982) or E. Block in S. Patai, *The Chemistry of Functional Groups*, Supplement E, Part 1, pages 539-608, John Wiley and Sons (Interscience Publication), 1980]. Illustrative oxidizing agents are all reagents usually employed for the oxidation of sulfides to sulfoxides, for example hypohalites, and in particular peroxyacids, such as peroxyacetic acid, trifluoroperoxyacetic acid, 3,5-dinitroperoxybenzoic acid, peroxymaleic acid or, preferably, m-chloroperoxybenzoic acid.

The (oxidation) reaction temperature is between −70° C. and the boiling point of the solvent used (depending on the reactivity of the oxidizing agent and the degree of dilution), but preferably between −50° and +20° C. The oxidation is advantageously carried out in inert solvents, for example aromatic or chlorinated hydrocarbon, such as benzene, toluene, dichloromethane or chloroform; esters, such as ethyl acetate or isopropyl acetate; or ethers, such as dioxane, with the addition of water or without water.

The reaction of IX with X is preferably carried out in an inert solvent usually employed for the reaction of enolate ions with alkylating agents. Examples include aromatic solvents, such as benzene or toluene. The reaction temperature is as a rule between 0° and 120° C. (depending on the nature of the alkali-metal atom M and the leaving group Z), the boiling point of the solvent used being preferred. For example [if M represents Li (lithium) and Z represents Cl (chlorine) and the reaction is carried out in benzene], the boiling point of benzene (80° C.) is preferred.

The compounds XI are reacted with compounds XII in a conventional manner and under known conditions suitable for the reaction of organometallic compounds.

Depending on the nature of the starting compounds, which can optionally also be employed as salts, and depending on the reaction conditions, the compounds according to the invention are initially obtained either as free compounds or in the form of salts.

The salts are obtained by dissolving the free compounds in a suitable solvent, for example in a chlorinated hydrocarbon, such as methylene chloride or chloroform, a low molecular weight aliphatic alcohol (ethanol or isopropanol), an ether (diisopropyl ether), a ketone (acetone) or water, which contains the desired acid or base, or to which the desired acid or base is added (if necessary) in the precisely calculated stoichiometric amount.

The salts are obtained by filtration, reprecipitation, or precipitation or by evaporation of the solvent.

Resulting salts are converted into the free compounds by treatment with bases or acids, for example with aqueous sodium bicarbonate or with dilute hydrochloric acid, and the free compounds are optionally converted into their salts. In this manner, the compounds are purified, or pharmacologically-unacceptable salts are converted into pharmacologically-acceptable salts.

The sulfoxides according to the invention are optically active compounds. The invention therefore relates both to the enantiomers and to their mixtures and racemates. The enantiomers are separated by known methods (for example, by preparation and separation of corresponding diastereoisomers). However, the enantiomers are also prepared by asymmetric synthesis, for example by reaction of optically-active pure or diastereoisomerically pure compounds XI with compounds XII [cf. K. K. Andersen, *Tetrahedron Lett.*, 93 (1962)].

The compounds according to the invention are preferably synthesized by reaction of II with III and, if appropriate, subsequent oxidation of the sulfide VIII formed.

The compounds of the formula II are known (cf. German Offenlegungsschrift No. 3,132,613) and are prepared by known methods from known starting materials. Compounds II are obtained, for example, by reacting compounds VI with carbon disulfide in the presence of alkali-metal hydroxides or with alkali-metal O-ethyl dithiocarbonates.

Compounds of formula VI are synthesized in a known manner by the general preparation methods described in the following equation A:

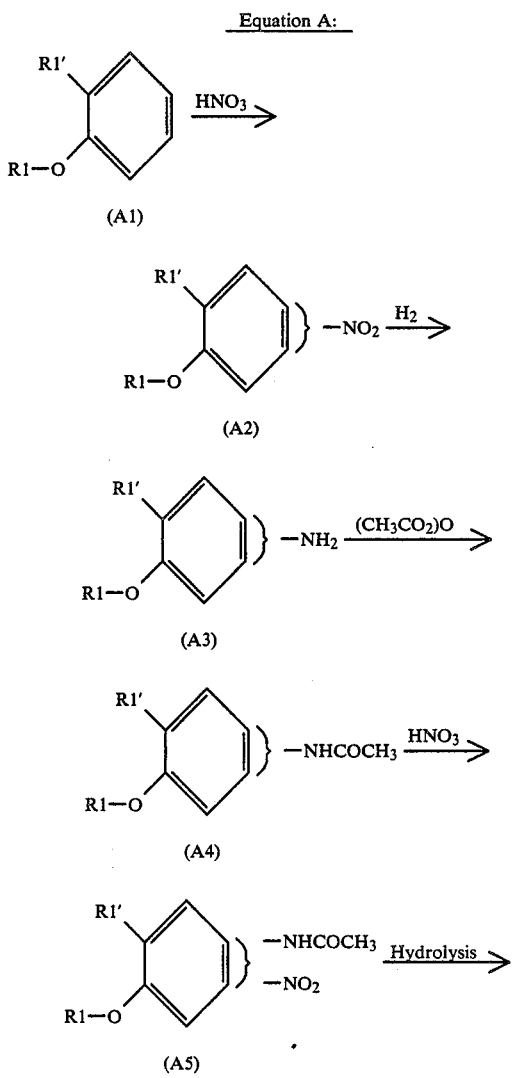

-continued

Equation A:

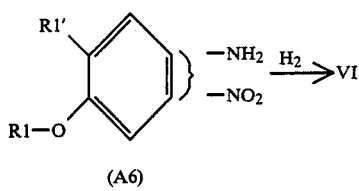

(A6)

The starting compounds A1–A3 are prepared by known methods or by methods analogous to the following: [cf. *J. Org. Chem.* 44, 2907–2910 (1979); *J. Org. Chem.* 29, 1–11 (1964); German Offenlegungsschrift No. 2,029,556; German Offenlegungsschrift No. 2,848,531; *J. Fluorine Chem.* 18, 281–91 (1981); and *Synthesis* 1980, 727–8]. Optionally, isomer mixtures are prepared in the case of non-identical substituents R1' and R1-0-.

Compounds IV, IX and XI are conventionally prepared, for example, from compounds II.

Compounds IX are obtained, for example, from compounds II by methylation, oxidation and subsequent deprotonation, for example, with alkali-metal hydrides or alcoholates or customary organometallic compounds. Compounds X are prepared according to Z. Talik, *Roczniki chem.* 35, 475 (1961).

Compounds III are prepared in various ways:

1. Compounds III where R2 and R3=1–3C-alkoxy and R4=hydrogen or 1–3C-alkyl.

These compounds are prepared, for example, starting from 3-hydroxy- or 3-hydroxy-5-alkyl-pyridines (which are known or are conventionally prepared from known starting materials) by benzylation of the hydroxyl group (for example with potassium hydroxide and benzyl chloride in dimethyl sulfoxide), N-oxidation (for example with 30% strength hydrogen peroxide), nitration in the 4-position (for example with nitrating acid), replacement of the nitro group by the 1–3C-alkoxy group (for example by reaction with alkali-metal alkoxide), reductive debenzylation and simultaneous N-deoxygenation (for example with hydrogen over palladium-on-charcoal in an acid medium), introduction of the hydroxymethyl group in the o-position relative to the pyridine nitrogen (for example by reaction with alkaline formalin solution), conversion of the 3-hydroxy group into a 1–3C-alkoxy group (for example by alkylation with 1–3C-alkyl iodide in a basic medium) and introduction of the leaving group Z' (for example by reaction with thionyl chloride). In a preferred alternative, the compounds are prepared starting from 3-hydroxy-2-alkyl- or 3-hydroxy-2,5-dialkyl-pyridines (which are known or are conventionally prepared) by alkylation of the hydroxyl group (for example with potassium hydroxide and methyl iodide in dimethyl sulfoxide), N-oxidation (for example with 30% strength hydrogen peroxide), nitration in the 4-position (for example with nitric acid), replacement of the nitro group by the 1–3C-alkoxy group (for example by reaction with alkali-metal alkoxide), conversion into the 2-acetoxymethylpyridine (for example with hot acetic anhydride), hydrolysis (for example with dilute sodium hydroxide solution) to the hydroxymethyl group and introduction of the leaving group Z' (for example by reaction with thionyl chloride).

2. Compounds III where R3 and R4=1–3C-alkoxy and R2=hydrogen.

These compounds are prepared, for example, starting from known 5-hydroxy-2-methylpyridines by alkylation of the hydroxyl group (for example with 1–3C-alkyl iodide and potassium hydroxide in dimethyl sulfoxide), N-oxidation (for example with 30% strength hydrogen peroxide), nitration in the 4-position (for example with nitrating acid), replacement of the nitro group by the 1–3C-alkoxy group (for example by reaction with alkali metal alkoxide), conversion into the 2-acetoxymethylpyridine (for example with hot acetic anhydride), hydrolysis (for example with dilute sodium hydroxide solution) to the 2-hydroxymethyl group and introduction of the leaving group Z' (for example by reaction with thionyl chloride).

3. Compounds III where R3 and R4=1–3C-alkoxy and R2=1–3C-alkyl.

These compounds are prepared, for example, starting from 2-methyl-3-alkyl-4-alkoxypyridines which are known or are conventionally prepared (see, for example, European Pat. No. A-0,080,602), by N-oxidation (for example with 30% strength hydrogen peroxide), controlled acetoxylation and subsequent hydrolysis in the 5-position (for example with acetic anhydride and subsequently sodium hydroxide solution), alkylation of the 5-hydroxy group (for example with 1–3C-alkyl iodide and sodium hydroxide solution in dimethyl sulfoxide), N-oxidation (for example with m-chloroperoxybenzoic acid), conversion into the 2-acetoxymethylpyridine (for example with hot acetic anhydride), hydrolysis (for example with dilute sodium hydroxide solution) to the 2-hydroxymethyl group and introduction of the leaving group Z' (for example by reaction with thionyl chloride).

The specific reaction conditions (temperatures, reaction times, solvents and the like) in the synthesis routes outlined above for the preparation of the compounds III are familiar to the artisan. The preparation of individual representatives of the compounds III is described in the examples. Other representatives are prepared analogously.

The compounds III, wherein R3 represents 1–3C-alkoxy, one of the radicals R2 and R4 represents a 1–3C-alkoxy radical and the other represents a 1–3C-alkyl radical are new and are also the subject of the invention.

The compounds V, VII and XII are prepared, for example, starting from the compounds III and by employing conventional routes.

The following examples illustrate the invention in more detail without limiting it. In the examples, m.p. denotes melting point, decomp. represents decomposition and b.p. represents boiling point.

EXAMPLES 1. 2-[(4,5-Dimethoxy-2-pyridyl)methylthio]-5-trifluoromethoxy-1H-benzimidazole 1.57 g of 2-chloromethyl-4,5-dimethoxypyridinium chloride are added to a solution of 1.64 g of 2-mercapto-5-trifluoromethoxy-1H-benzimidazole in 40 ml of ethanol and 20 ml of 1N sodium hydroxide solution, the mixture is stirred at 20° C. for 2 hours and then at 40° C. for a further hour, the ethanol is distilled off on a rotary evaporator (10 mbar/40° C.) and the colorless precipitate which thereby separates out is filtered off over a suction filter, rinsed with 1N sodium hydroxide solution and water and dried. 2.15 g (79% of theory) of the title compound of m.p. 92°–93° C. are obtained.

5-Chlorodifluoromethoxy-2-[(4,5-dimethoxy-2-pyridyl)methylthio]-1H-benzimidazole, 5-difluoromethoxy-2-[(4,5-dimethoxy-2-pyridyl)methylthio]-1H-benzimidazole (oil), 5,6-bis(difluoromethoxy)-2-[(4,5-dimethoxy-2-pyridyl)methylthio]-1H-benzimidazole, 5-difluoromethoxy-6-methoxy-2-[(4,5 dimethoxy-2-pyridyl)methylthio]-1H-benzimidazole (m.p. 159°–160° C.) and 5-difluoromethoxy-6-fluoro-2-[(4,5-dimethoxy-2-pyridyl)methylthio]-1H-benzimidazole are obtained analogously by reacting 5-chlorodifluoromethoxy-2-mercapto-1H-benzimidazole, 5-difluoromethoxy-2-mercapto-1H-benzimidazole, 5,6-bis(difluoromethoxy)-2-mercapto-1H-benzimidazole, 5-difluoromethoxy-2-mercapto-6-methoxy-1H-benzimidazole and 5-difluoromethoxy-6-fluoro-2-mercapto-1H-benzimidazole with 2-chloromethyl-4,5-dimethoxypyridinium chloride.

2. 2-[(4,5-Dimethoxy-2-pyridyl)methylsulfinyl]-5-trifluoromethoxy-1H-benzimidazole 5.5 ml of a 0.2M solution of m-chloroperoxybenzoic acid in methylene chloride are added dropwise to a solution of 0.36 g of 2-[4,5-dimethoxy-2-pyridyl)methylthio]-5-trifluoromethoxy-1H-benzimidazole in 10 ml of methylene chloride at −50° C. and the mixture is stirred at the stated temperature for a further 30 minutes. After addition of 0.3 ml of triethylamine, the cold reaction mixture is stirred into 10 ml of 5% strength sodium thiosulfate solution and 10 ml of 5% strength sodium carbonate solution. After phase separation three further extrations with 10 ml of methylene chloride are performed, the combined organic phases are washed once with 5 ml of 5% strength sodium thiosulfate solution and dried. The drying agent (magnesium sulfate) is filtered off and the filtrate is concentrated. The residue is crystallized with diisopropyl ether and is then reprecipitated from methylene chloride/diisopropyl ether. 0.27 g (72% of theoretical) of the title compound is obtained as a colorless solid of m.p. 159°–61° C. (decomp.).

5-Chlorodifluoromethoxy-2-[(4,5-dimethoxy-2-pyridyl)methylsulfinyl]-1H-benzimidazole, 5-difluoromethoxy-2-[(4,5-dimethoxy-2-pyridyl)methylsulfinyl]-1H-benzimidazole [m.p. 159° C. (decomp.)], 5,6-bis(difluoromethoxy)-2-[(4,5-dimethoxy-2-pyridyl)methylsulfinyl]-1H-benzimidazole, 5-difluoromethoxy-6-methoxy-2-[(4,5-dimethoxy-2-pyridyl)methylsulfinyl]-1H-benzimidazole and 5-difluoromethoxy-6-fluoro-2,2-[(4,5-dimethoxy-2-pyridyl)methylsulfinyl]-1H-benzimidazole are obtained analogously by oxidation of other sulfides of Example 1 with m-chloroperoxybenzoic acid.

3. 2-[(4,5-Dimethoxy-2-pyridyl)methylthio]-5-(1,1,2,2-tetrafluoroethoxy)-1H-benzimidazole 1.40 g of the title compound are obtained as a yellow oil by the procedure described in Example 1, by reacting 1.07 g of 2-mercapto-5-(1,1,2,2-tetrafluoroethoxy)-1H-benzimidazole with 0.90 g of 2-chloromethyl-4,5-dimethoxypyridinium chloride in 15 ml of ethanol with the addition of 17 ml of 0.5N sodium hydroxide solution. Recrystallization from petroleum ether yields 1.20 g (72% of theoretical) of the desired compound as colorless crystals of m.p. 125°–127° C.

4. 2-[(4,5-Dimethoxy-2-pyridyl)methylsulfinyl]-5-(1,1,2,2-tetrafluoroethoxy)-1H-benzimidazole A solution of the product in methylene chloride is obtained by the procedure described in Example 2 by oxidation of 0.76 g of 2-[(4,5-dimethoxy-2-pyridyl)methylthio]-5-(1,1,2,2-tetrafluoroethoxy)-1H-benzimidazole with 19 ml of a 0.1M solution of m-chloroperoxybenzoic acid in 30 ml of methylene chloride at −40° C., after extraction. After drying the solution over magnesium sulfate, the drying agent is filtered off, the filtrate is concentrated and the residue is crystallized from methylene chloride/diisopropyl ether. 0.64 g (82% of theory) of the title compound is obtained in the form of colorless crystals of m.p. 160°–162° C. (decomp.).

5. 2-[(4,5-Dimethoxy-2-pyridyl)methylthio]-5-(2,2,2-trifluoroethoxy)-1H-benzimidazole 1.0 g of 2-mercapto-5-(2,2,2-trifluoroethoxy)-1H-benzimidazole is dissolved in 15 ml of ethanol and 8.5 ml of 1N sodium hydroxide solution, 0.90 g of 2-chloromethyl-4,5-dimethoxypyridinium chloride are added and the mixture is stirred for 20 hours. After addition of 30 ml of water, the mixture is extracted three times with 30 ml of methylene chloride each time, the methylene chloride phase is washed once with 5 ml of 0.1N sodium hydroxide solution, the combined organic phases are dried over magnesium sulfate and, after the drying agent has been filtered off, the filtrate is completely concentrated. 1.51 g (94% of theory) of the title compound are obtained as an amorphous solid residue of m.p. 55°–57° C.

6. 2-[(4,5-Dimethoxy-2-pyridyl)methylsulfinyl]-5-(2,2,2-trifluoroethoxy)-1H-benzimidazole 0.8 g of 2-[(4,5-dimethoxy-2-pyridyl)methylthio]-5-(2,2,2-trifluoroethoxy)-1H-benzimidazole is dissolved in 15 ml of dioxane and 2.5 ml of 1N sodium hydroxide solution. A mixture of 3 ml of 8% strength sodium hypochlorite solution and 3.5 ml of 1N sodium hydroxide solution are added dropwise in the course of 2 hours, while cooling to 0°–5° C. After addition of 5 ml of 5% strength sodium thiosulfate solution, the mixture is concentrated to dryness, the residue is taken up in water and the mixture is brought to pH 7 with phosphate buffer. The solid which has precipitated out is filtered off with suction, dried and recrystallized from ethyl acetate/diisopropyl ether. 0.45 g (55% of theory) of the title compound is obtained as colorless crystals of m.p. 142°–143° C. (decomp.).

7. 2-[(4,5-Dimethoxy-3-methyl-2-pyridyl)methylthio]-5-(1,1,2,2-tetrafluoroethoxy)-1H-benzimidazole 1.46 g (83% of theory) of the title compound of m.p. 127°–128° C. (colorless powder) are obtained by the procedure described in Example 1 by reaction of 1.07 g of 2-mercapto-5-(1,1,2,2-tetrafluoroethoxy)-1H-benzimidazole with 0.96 g of 2-chloromethyl-4,5-dimethoxy-3-methylpyridinium chloride in 12 ml of ethanol, with the addition of 17 ml of 0.5N sodium hydroxide solution.

8. 2-[(4,5-Dimethoxy-3-methyl-2-pyridyl)methylsulfinyl]-5-(1,1,2,2-tetrafluoroethoxy)-1H-benzimidazole 0.8 g of a pale yellow oil is obtained by the procedure described in Example 2 by oxidation of 0.99 g of 2-[(4,5-dimethoxy-3-methyl-2-pyridyl)methylthio]-5-(1,1,2,2-tetrafluoroethoxy)-1H-benzimidazole with 12 ml of a 0.2M solution of m-chloroperoxybenzoic acid in methylene chloride at −40° C. for a reaction time of 1.5 hours. Recrystallization twice from methylene chloride/diisopropyl ether gives 0.30 g (34% of theory) of the title compound in the form of colorless crystals of m.p. 125° C. (decomp.).

9. 5-Difluoromethoxy-2-[(4,5-dimethoxy-3-methyl-2-pyridyl)methylthio]-1H-benzimidazole 0.64 g (84% of theory) of the title compound of m.p. 100°–102° C. (colorless crystalline powder) is obtained by the procedure described in Example 'by reaction of 0.38 g (2 mmol) of 5-difluoromethoxy-2-mercapto-1H- benzimidazole with 0.48 g (2 mmol) of 2-chloromethyl-4,5-dimethoxy-3-methylpyridinium chloride in 10 ml of ethanol, with the addition of 8.8 ml of 1N sodium hydroxide solution, after two hours at 50° C.

10. 2-[(3,4-Dimethoxy-2-pyridyl)methylthio]-5-(1,1,2,2-tetrafluoroethoxy)-1H-benzimidazole 0.38 g (1.7 mmol) of 2-chloromethyl-3,4-dimethoxypyridinium chloride is added to a solution of 0.46 g (1.7 mmol) of 2-mercapto-5-(1,1,2,2-tetra fluoroethoxy)-1H-benzimidazole in 10 ml of ethanol, 10 ml of water and 1.8 ml of 2N sodium hydroxide solution; after the mixture has been stirred at 20° C. for one hour, a further 10 ml of water are added dropwise. The mixture is then stirred at 20° C. for a further four hours. The solid which has precipitated out is filtered off, washed with 0.01N sodium hydroxide solution and then with water until neutral and dried to constant weight. 0.63 g (90% of theory) of the title compound is obtained as a colorless crystalline powder of m.p. 98°–102° C.

5-Difluoromethoxy-2-[(3,4-dimethoxy-2-pyridinyl-methylthio)]-1H-benzimidazole (m.p. 104°–108° C.) and 5-difluoromethoxy-6-methoxy-2-[(3,4-dimethoxy-2-pyridylmethylthio)]-1H-benzimidazole (m.p. 137°–138° C.) are obtained analogously by reacting 5-difluoromethoxy-2-mercapto-1H-benzimidazole and 5-difluoromethoxy-6-methoxy-2-mercapto-1H-benzimidazole with 2-chloromethyl-3,4-dimethoxypyridinium chloride.

11. 2-[(4,5-Dimethoxy-3-methyl-2-pyridyl)methylthio]-5-trifluoromethoxy-1H-benzimidazole 1.40 g (70% of theory) of the title compound are obtained by the procedure described in Example 1 by reaction of 1.15 g of 2-mercapto-5-trifluoromethoxy-1H-benzimidazole with 1.20 g of 2-chloromethyl-4,5-dimethoxy-3-methylpyridinium chloride in 20 ml of isopropanol, with the addition of 20.5 ml of 0.5N sodium hydroxide solution. Recrystallization from diisopropyl ether/petroleum ether gives a product of m.p. 94°–97° C.

2-[(4,5-Dimethoxy-3-methyl-2-pyridyl)methylthio]-5-(2,2,2-trifluoro ethoxy)-1H-benzimidazole, 5-chlorodifluoromethoxy-2-[(4,5-dimethoxy-3-methyl-2-pyridyl)methylthio]-1H-benzimidazole, 5,6-bis(difluoromethoxy)-2-[(4,5-dimethoxy-3-methyl-2-pyridyl)methylthio]-1H-benzimidazole, 5-difluoromethoxy-6-methoxy-2-[(4,5-dimethoxy-3-methyl-2-pyridyl)methylthio]-1H-benzimidazole and 5-difluoromethoxy-6-fluoro-2-[(4,5-dimethoxy-3-methyl-2-pyridyl)methylthio]-1H-benzimidazole are obtained analogously by reacting 2-mercapto-5-(2,2,2-trifluoroethoxy-1H-benzimidazole, 5-chlorodifluoromethoxy-2-mercapto-1H-benzimidazole, 5,6-bis(difluoromethoxy)-2-mercapto-1H-benzimidazole, 5-difluoromethoxy-2-mercapto-6-methoxy-1H-benzimidazole and 5-difluoromethoxy-6-fluoro-2-mercapto-1H-benzimidazole, respectively, with 2-chloromethyl-4,5-dimethoxy-3-methylpyridinium chloride.

12. 2-[(4,5-Dimethoxy-3-methyl-2-pyridyl)methylsulfinyl]-5-trifluoromethoxy-1H-benzimidazole 0.19 g (76% of theory) of the title compound is obtained as a colorless powder (158°–159° C. decomp.) by the procedure described in Example 2 by oxidation of 0.24 g of 2-[(4,5-dimethoxy-3-methyl-2-pyridyl)methylthio]-5-trifluoromethoxy-1H-benzimidazole with 3.3 ml of a 0.2M solution of m-chloroperoxybenzoic acid in methylene chloride at −50° C. and reprecipitation from methylene chloride/diisopropyl ether.

2-[(4,5-Dimethoxy-3-methyl-2-pyridyl)methylsulfinyl]-5-(2,2,2-trifluoroethoxy)-1H-benzimidazole, 5-chlorodifluoromethoxy-2-[(4,5-dimethoxy-3-methyl-2-pyridyl)methylsulfinyl]-1H-benzimidazole, 5-difluoromethoxy-2-[(4,5-dimethoxy-3-methyl-2-pyridyl)methylsulfinyl]-1H-benzimidazole [m.p. 133°–135° C. (decomp.)], 5,6-bis(difluoromethoxy)-2-[(4,5-dimethoxy-3-methyl-2-pyridyl)methylsulfinyl]-1H-benzimidazole, 5-difluoromethoxy-6-methoxy-2-[(4,5-dimethoxy-3-methyl-2-pyridyl)methylsulfinyl]-1H-benzimidazole, 5-difluoromethoxy-6-fluoro-2-[(4,5-dimethoxy-3-methyl-2-pyridyl)methylsulfinyl]-1H-benzimidazole and 2-[(3,4-dimethoxy-2-pyridyl)methylsulfinyl]-5-(1,1,2,2-tetrafluoroethoxy)-1H-benzimidazole [m.p. 117°–119° C. (decomp.)] and 5-difluoromethoxy-2-[(3,4-dimethoxy-2-pyridyl)methylsulfinyl]-1H-benzimidazole [m.p. 136° C. (decomp.)] are obtained analogously by oxidation of the sulfides of Examples 9 to 11 with m-chloroperoxybenzoic acid.

13. 2,2-Difluoro-6-[(4,5-dimethoxy-3-methyl-2-pyridyl)methylthio]-5H-[1,3]-dioxolo[4,5-f]benzimidazole 0.96 g of 2-chloromethyl-4,5-dimethoxy-3-methylpyridinium chloride are added to a solution of 0.92 g of 2,2-difluoro-5H-[1,3]-dioxolo[4,5-f]benzimidazole-6-thiol in 10 ml of ethanol and 10 ml of 1N sodium hydroxide solution. The yellow reaction mixture is stirred at 20° C. for 1 hour, a further 10 ml of water are added, whereupon a colorless solid precipitates out, the mixture is stirred for a further 5 hours and filtered and the residue is rinsed with 1N sodium hydroxide solution and water and dried to constant weight. The amorphous powder is recrystallized from methylene chloride/diisopropyl ether. 1.5 g (93% of theory) of the title compound are obtained in the form of colorless crystals of m.p. 160°–161° C.

6,6,7-Trifluoro-6,7-dihydro-2-[(4,5-dimethoxy-3-methyl-2-pyridyl)methylthio]-1H-[1,4]dioxino[2,3-f]benzimidazole, 6-chloro-6,7,7-trifluoro-6,7-dihydro-2-[(4,5-dimethoxy-3-methyl-2-pyridyl)methylthio]-1H-[1,4]-dioxino[2,3-f]benzimidazole and 6,7-dihydro-2-[(4,5-dimethoxy-3-methyl-2-pyridyl)methylthio]-1H-[1,4]-dioxino[2,3-f]-benzimidazole are obtained analogously by reacting 6,6,7-trifluoro-6,7-dihydro-1H-[1,4]-dioxino[2,3-f]benzimidazole-2-thiol, 6-chloro-6,7,7-trifluoro-6,7-dihydro-1H-[1,4]-dioxino[2,3-f]benzimidazole-2-thiol or 6,7-dihydro-1H-[1,4]-dioxino[2,3-f]benzimidazole-2-thiol, respectively, with 2-chloromethyl-4,5-dimethoxy-3-methylpyridinium chloride.

14. 2,2-Difluoro-6-[(4,5-dimethoxy-3-methyl-2-pyridyl)methylsulfinyl]-5H-[1,3]-dioxolo[4,5-f]benzimidazole 21 ml of a 0.1N solution of m-chloroperoxybenzoic acid in methylene chloride are added dropwise to a suspension, cooled to −40° C., of 0.80 g of 2,2-difluoro-6[(4,5-dimethoxy-3-methyl-2-pyridyl)methylthio]-5H-[1,3]-dioxolo[4,5-f]-benzimidazole in 10 ml of methylene chloride in the course of 10 minutes. The mixture is stirred for a further 20 minutes, during which the temperature is allowed to rise to −20° C., and 0.5 ml of triethylamine are added and the reaction mixture is poured into 40 ml of 5% strength sodium thiosulfate solution and 5% strength sodium carbonate solution. After phase separation, the aqueous phase is extracted twice more with 20 ml of methylene chloride each time; the combined organic phases are washed with a mixture of 5 ml of sodium thiosulfate solution and 5 ml of sodium carbonate solution, dried and concentrated. The residue is recrystallized from methylene chloride/diisopropyl ether. 0.62 g (75% of theory) of the title compound is obtained; decomp. 189°–190° C.

6,6,7-Trifluoro-6,7-dihydro-2-[(4,5-dimethoxy-3-methyl-2-pyridyl)methylsulfinyl]-1H-[1,4]-dioxino[2,3-f]benzimidazole, 6-chloro-6,7,7-trifluoro-6,7-dihydro-2-[(4,5-dimethoxy-3-methyl-2-pyridyl)methylsulfinyl]-1H-[1,4]-dioxino[2,3-f]benzimidazole and 6,7-dihydro-2-[(4,5-dimethoxy-3-methyl-2-pyridyl)methylsulfinyl]-1H-[1,4]-dioxino[2,3-f]benzimidazole are obtained analogously by oxidation of the other sulfides mentioned under Example 13 with m-chloroperoxybenzoic acid.

15. 6-[(4,5-Dimethoxy-2-pyridyl)methylthio]-5H-[1,3]-dioxolo[4,5-f]benzimidazole A brownish solid is obtained by the procedure described in Example 13 by reaction of 0.85 g of 5H-[1,3]-dioxolo[4,5-f]-benzimidazole-6-thiol with 0.98 g of 2-chloromethyl-4,5-dimethoxypyridinium chloride in 10 ml of ethanol and 10 ml of water, with the addition of 8.5 ml of 1N sodium hydroxide solution, after a reaction time of 20 hours and after concentration, by removing the solvent in vacuo, to a volume of 10 ml. The crude product is dissolved in 30 ml of methylene chloride, the solution is clarified with fuller's earth (for example, Tonsil ®), and concentrated. The residue is crystallized by addition of diisopropyl ether and the now pale yellow solid is boiled up in 5 ml of methanol. 0.90 g (60% of theory) of the title compound is obtained as a colorless solid of m.p. 198°–200° C.

16. 6-[(4,5-Dimethoxy-2-pyridyl)methylsulfinyl]-5H-[1,3]-dioxolo[4,5-f]-benzimidazole 0.27 g of the title compound in the form of colorless crystals of m.p. 199° C. (decomp.) is obtained by the procedure described in Example 14 by oxidation of 0.7 g of 6-[(4,5-dimethoxy-2-pyridyl)methylthio]-5H-[1,3]-dioxolo[4,5-f]-benzimidazole with 23 ml of a 0.1M solution of m-chloroperoxybenzoic acid, after recrystallization from diethyl ether.

17. 2,2-Difluoro-6-[(3,4-dimethoxy-2-pyridyl)methylthio]-5H-[1,3]-dioxolo[4,5-f]benzimidazole 1.05 g (92% of theory) of the title compound are obtained as a finely crystalline, colorless powder of m.p. 185°–187° C. by the procedure described in Example 13 by reaction of 0.69 g (3 mmol) of 2,2-difluoro-5H-[1,3]dioxolo[4,5-f]benzimidazole-6-thiol with 0.67 g (3 mmol) of 2-chloromethyl-3,4-dimethoxypyridinium chloride in a mixture of 10 ml of ethanol and 10 ml of water, with the addition of 3.3 ml of 2N sodium hydroxide solution, after a reaction time of 10 hours.

6-[(3,4-Dimethoxy-2-pyridyl)methylthio]-5H-[1,3]-dioxolo[4,5-f]benzimidazole (m.p. 155°–157° C.) is obtained analogously by reacting 5H-[1,3]-dioxolo[4,5-f]benzimidazole-6-thiol with 2-chloromethyl-3,4-dimethoxypyridinium chloride.

18. 6-[(4,5-Dimethoxy-3-methyl-2-pyridyl)methylthio]-5H-[1,3]-dioxolo[4,5-f]benzimidazole 0.78 g (4 mmol) of 5H-[1,3]-dioxolo[4,5-f]benzimidazole-6-thiol is heated at the boiling point under reflux with 0.95 g (4 mmol) of 2-chloromethyl-4,5-dimethoxy-3-methylpyridinium chloride in 30 ml of isopropanol for 15 hours. The solid which has precipitated out is filtered off and extracted by stirring with isopropanol, the mixture is filtered again and the residue is dried to constant weight. 1.0 g (59% of theory) of the dihydrochloride of the title compound is obtained as a colorless solid of m.p. 206° C. (decomp.).

19. 2,2-Difluoro-6-[(4,5-dimethoxy-2-pyridyl)methylthio]-5H-[1,3]-dioxolo[4,5-f]benzimidazole 6.3 ml of 1N sodium hydroxide solution are added dropwise to a solution, warmed to 50° C., of 0.69 g of 2,2-difluoro-5H-[1,3]dioxolo[4,5-f]benzimidazole-6-thiol and 0.67 g of 2-chloromethyl-4,5-dimethoxypyridinium chloride in 9 ml of ethanol and 4 ml of water in the course of one minute. On cooling the clear reaction mixture to 20° C., a colorless precipitate separates out after a short time. The mixture is stirred at 20° C. for a further 5 hours and the precipitate is filtered off with suction over a suction filter, rinsed with 1N sodium hydroxide solution and water and dried to constant weight. The beige solid is dissolved in 10 ml of methylene chloride, insoluble constituents are filtered off, the filtrate is concentrated and the residue is made to crystallize by addition of diisopropyl ether after cooling. 1.02 g (90% of theory) of the title compound of m.p. 189°–191° C. are obtained.

6,6,7-Trifluoro-6,7-dihydro-2-[(4,5-dimethoxy-2-pyridyl)methylthio]-1H-[1,4]-dioxino[2,3-f]benzimidazole, 6-chloro-6,7,7-trifluoro-6,7-dihydro-2-[(4,5-dimethoxy-2-pyridyl)methylthio]-1H-[1,4]-dioxino[2,3-f]benzimidazole and 6,7-dihydro-2-[(4,5-dimethoxy-2-pyridyl)methylthio]-1H-[1,4]-dioxino[2,3-f]benzimidazole are obtained analogously by reacting 6,6,7-trifluoro-6,7-dihydro-1H-[1,4]dioxino[2,3-f]-benzimidazole-2-thiol, 6-chloro-6,7,7-trifluoro-6,7-dihydro-1H-[1,4]-dioxino[2,3-f]benzimidazole-2-thiol or 6,7-dihydro-1H-[1,4]-dioxino[2,3-f]benzimidazole-2-thiol (respectively) with 2-chloromethyl-4,5-dimethoxypyridinium chloride.

20. 2,2-Difluoro-6-[(4,5-dimethoxy-2-pyridyl)methylsulfinyl]-5H-[1,3]-dioxolo[4,5-f]benzimidazole 0.76 g of 2,2-difluoro-6-[(4,5-dimethoxy-2-pyridyl)methylthio]-5H-[1,3]-dioxolo[4,5-f]benzimidazole are dissolved in 10 ml of dioxane and 2 ml of 1N sodium hydroxide solution. An equimolar amount of a titrated aqueous sodium hypochlorite solution, to which 1 mole per liter of sodium hydroxide solution has been added, is first added dropwise, while cooling with ice, and after one hour a further equivalent and after 3 hours half the equimolar amount of sodium hypochlorite are added, to achieve complete reaction. After a reaction time of 4 hours, 5 ml of 5% strength sodium thiosulfate solution and another 25 ml of dioxane are added and the upper dioxane phase is separated off, washed once with 5 ml of sodium thiosulfate solution and concentrated on a rotary evaporator. The oily residue is dissolved in 20 ml of water and 10 ml of ethyl acetate and the solution is brought to pH 7 with about 100 ml of a buffer solution of pH 6.8. The solid which has precipitated out is filtered off with suction over a suction filter, washed with water, extracted by stirring at 0° C. with acetone and dried. 0.7 g (87% of theory) of the title compound is obtained in the form of colorless crystals; decomp. at 211°–213° C.

2,2-Difluoro-6-[(3,4-dimethoxy-2-pyridyl)methylsulfinyl]-5H-[1,3]-dioxolo[4,5-f]benzimidazole [m.p. 177°–178° C. (decomp.)], 6-[(4,5-dimethoxy-3-methyl-2-pyridyl)methylsulfinyl]-5H-[1,3]-dioxolo[4,5-f]benzimidazole, 6,6,7-trifluoro-6,7-dihydro-2-[4,5-dimethoxy-2-pyridyl)methylsulfinyl]-1H-[1,4]-dioxino[2,3-f]benzimidazole, 6-[(3,4-dimethoxy-2-pyridyl)methylsulfinyl]-5H-[1,3]-dioxolol[4,5-f]benzimidazole [m.p. 170°–171° C. (decomp.)], 6-chloro-6,7,7-trifluoro-6,7-dihydro-2-[(4,5-dimethoxy-2-pyridyl)methylsulfinyl]-1H-[1,4]-dioxino-[2,3-f]benzimidazole and 6,7-dihydro-2-[(4,5-dimethoxy-2-pyridyl)methylsulfinyl]-1H-[1,4]-dioxino[2,3-f]-benzimidazole are obtained analogously by oxidation of the other sulfides mentioned in Examples 17 to 19 with sodium hypochlorite solution.

21. 2-Mercapto-5-(1,1,2,2-tetrafluoroethoxy)-1H-benzimidazole (a) 55 g of 1-nitro-4-(1,1,2,2-tetrafluoroethoxy)-benzene are hydrogenated in 300 ml of ethanol over 0.5 g of 10% strength palladium-on-charcoal in a circulatory hydrogenation apparatus under atmospheric pressure at 20°–45° C. for 1 hour, the catalyst is filtered off and the solution is concentrated in vacuo at 40° C. The 4-(1,1,2,2-tetrafluoroethoxy)aniline is diluted with 100 ml of glacial acetic acid, 23 ml of acetic anhydride are added dropwise at room temperature, 2 ml of water are added after 30 minutes, the solution is concentrated at 50° C. in vacuo after a short time and 500 ml of icewater are added. 56 g (97% of theoretical) of N-[4-(1,1,2,2-tetrafluoroethoxy)phenyl]-acetamide of m.p. 121°–122° C. are obtained.

(b) 55 g of the above compound are dissolved in 380 ml of dichloromethane, 55 ml of 100% strength nitric acid are added dropwise at room temperature in the course of 10 minutes and the mixture is stirred for a further 6 hours. The organic solution is then washed with aqueous sodium carbonate solution and water, dried with magnesium sulfate and concentrated. 65 g (100% of theoretical) of N-[2-nitro-4-(1,1,2,2-tetrafluoroethoxy)phenyl]-acetamide of m.p. 80°–81° C. (from cyclohexane) are obtained.

(c) 63 g of the above compound are dissolved in 450 ml of methanol, 106 ml of 6M sodium hydroxide solution are added dropwise at room temperature, the mixture is cooled in an ice-bath and 53 g (98% of theoretical) of 2-nitro-4-(1,1,2,2-tetrafluoroethoxy)-aniline (m.p. 85°–86° C.) are precipitated by dropwise addition of 900 ml of water.

(d) 33 g of the above compound are hydrogenated in about 600 ml of isopropanol over 1 g of 10% strength palladium-on-charcoal in a circulatory hydrogenation apparatus under normal pressure at room temperature. The catalyst is filtered off with suction and 34 g (89%) of 4-(1,1,2,2-tetrafluoroethoxy)-1,2-phenylenediamine dihydrochloride of m.p. 275°–276° C. (decomposition) are precipitated with 4M hydrogen chloride in ether.

(e) 330 ml of ethanol, 60 ml of water, 8.9 g of sodium hydroxide and 23 g of potassium o-ethyldithiocarbonate (recrystallized from isopropanol) are added to 33 g of the above compound and the mixture is heated at the boiling point under reflux for 15 hours. 1.2 l of ice-water are added, the pH is brought to 13–14 with sodium hydroxide solution and the mixture is clarified with active charcoal and precipitated with dilute hydrochloric acid to pH 3.5. 27 g (91%) of the title compound of m.p. 316°–319° C. (from isopropanol) are obtained.

22. 2-Mercapto-5-trifluoromethoxy-1H-benzimidazole

The title compound of m.p. 305°–307° C. (decomposition, from toluene) is obtained in 75% yield analogously to Example 21(e) by reaction of 4-trifluoromethoxy-1,2-phenylenediamine dihydrochloride (compare C.A. 55, 23408d, 1961) with potassium O-ethyldithiocarbonate and sodium hydroxide solution in ethanol.

23. 2-Mercapto-5-(2,2,2-trifluoroethoxy)-1H-benzimidazole (a) 50 g of 1-(2,2,2-trifluoroethoxy)-4-nitrobenzene (*Synthesis* 1980, page 727) are hydrogenated and acetylated analogously to Example 21(a). 50 g (95%) of N-[4-(2,2,2-trifluoroethoxy)phenyl]acetamide (m.p. 140°–141° C.) are obtained.

(b) 42 g of the above compound are stirred with 9.7 ml of 100% strength nitric acid in 290 ml of glacial acetic acid at room temperature for 18 hours and the mixture is precipiated with water. 47 g (94%) of N-[2-nitro-4-(2,2,2-trifluoroethoxy)phenyl]-acetamide (m.p. 117°–118° C.) are obtained.

(c) 47 g of the above compound are hydrolyzed analogously to Example 21(c) to give 38.7 g (97%) of 2-nitro-4-(2,2,2-trifluoroethoxy)-aniline (m.p. 84°–85° C.).

(d) 37 g of the above compound are hydrogenated analogously to Example 21(d) to give 41 g (94%) of 4-(2,2,2-trifluoroethoxy)-1,2-phenylenediamine dihydrochloride of m.p. 230°–233° C. (decomposition).

(e) 30 g (94%) of the title compound (m.p. 288°–290° C.) are obtained analogously to Example 21(e) from 36 g of the above compound.

24. 5-Chlorodifluoromethoxy-2-mercapto-1H-benzimidazole (a) 10.0 g of N-[4-(chlorodifluoromethoxy)phenyl]acetamide (m.p. 101°–103° C., from 4-chlorodifluoromethoxyaniline and acetic anhydride) and 12.3 ml of 100% strength nitric acid are stirred in 80 ml of dichloromethane at 20° C. for 4 hours. The mixture is neutralized with aqueous potassium bicarbonate solution and the organic layer is concentrated to give 11.4 g (96%) of N-(4-chlorodifluoromethoxy-2-nitrophenyl)-acetamide (m.p. 89°–91° C.).

(b) 8.6 ml of a 30% strength solution of sodium methylate in methanol are added dropwise to 10.5 g of the above compound in 200 ml of methanol at 5° C., the mixture is stirred for 2 hours, without cooling, ice-water is added and the pH is brought to 8 to give 8.7 g (97%) of 4-chlorodifluoromethoxy-2-nitroaniline (m.p. 40°–42° C.).

(c) 8.5 g of the above compound are hydrogenated over 0.8 g of 10% strength palladium-on-charcoal under normal pressure in 200 ml of methanol, concentrated hydrochloric acid is added, the mixture is filtered, the filtrate is concentrated and the residue is stirred with diisopropyl ether. 8.5 g (97%) of 4-chlorodifluoromethoxy-1,2-phenylenediamine dihydrochloride are obtained.

(d) 6.3 g (72%) of the title compound of m.p. 268°–270° C. (decomposition) are obtained from 8.5 g of the above compound analogously to Example 21(e).

25. 5-Difluoromethoxy-2-mercapto-1H-benzimidazole (a) 11.8 g of N-(4-difluoromethoxyphenyl)-acetamide [L. M. Jagupol'skii et al., *J. General Chemistry* (USSR) 39, 190 (1969)] are stirred in 200 ml of dichloromethane with 12.1 ml of 100% strength hydrochloric acid at room temperature for 1.5 hours. 13.3 g (92%) of N-[(4-difluoromethoxy-2-nitro)phenyl]-acetamide (m.p. 71°–73° C.) are obtained analogously to Example 21(b).

(b) 4-Difluoromethoxy-2-nitroaniline (m.p. 68°–70° C.) is obtained therefrom in 96% yield analogously to Example 24(b).

(c) 4-Difluoromethoxy-1,2-phenylenediamine dihydrochloride is obtained therefrom in 94% yield analogously to Example 24(c).

(d) The title compound of m.p. 250°–252° C. (from isopropanol) is obtained in 78% yield analogously to Example 24(e).

26. 5,6-Bis(difluoromethoxy)-2-mercapto-1H-benzimidazole (a) 275 g of chlorodifluoromethane are passed into a solution of 100 g of pyrocatechol, 220 g of sodium hydroxide and 60 g of sodium dithionite in 500 ml of water and 400 ml of dioxane at 50°–55° C. analogously to L. N. Sedova et al., Zh. Org. Khim. 6, 568 (1970). After distillation at 61°–62° C./1.0–1.1 kPa, a mixture of 1,2-bis(difluoromethoxy)benzene and 2-difluoromethoxyphenol is obtained, the products being separated by chromatography on silica gel by means of cyclohexane/ethyl acetate (4:1).

(b) A solution of 15 g of 1,2-bis(difluoromethoxy)-benzene and 15 ml of 100% strength nitric acid in 150 ml of dichloromethane is stirred at room temperature for 7 hours. The mixture is neutralized with potassium bicarbonate solution and the organic layer is separated off and chromatographed on silica gel by means of cyclohexane/ethyl acetate (4:1). 1,2-Bis-(Difluoromethoxy)-4-nitro-benzene is obtained. This is hydrogenated and acetylated analogously to Example 21a to give N-[3,4-bis(difluoromethoxy)-phenyl]acetamide (m.p. 81°–83° C.). Analogously to Example 21, furthermore, N-[4,5-bis(difluoromethoxy)-2-nitrophenyl]acetamide (m.p. 65°–67° C.), N-[4,5-bis(difluoromethoxy)-2-nitro]aniline (m.p. 107°–109° C.), 4,5-bis(difluoromethoxy)-1,2-phenylenediamine dihydrochloride and the title compound of m.p. 285°–287° C. (decomposition; from isopropanol) are obtained.

27. 5-Difluoromethoxy-2-mercapto-6-methoxy-1H-benzimidazole (a) About 58 g of chlorodifluoromethane are passed into a solution of 55.5 g of guaiacol and 130 g of sodium hydroxide in 300 ml of water and 300 ml of dioxane at 60° C. The mixture is filtered at 10° C. and the organic layer is separated off, dried with anhydrous potassium carbonate and distilled. 56 g (73%) of 1-difluoromethoxy-2-methoxybenzene of boiling point 75°–76° C./0.9 kPa are obtained.

(b) A solution of 33.8 ml of 100% strength nitric acid in 90 ml of dichloromethane is added dropwise to a solution of 47 g of the above compound in 230 ml of dichloromethane at 0°–5° C., 250 ml of ice-water are added after 30 minutes and the mixture is neutralized with potassium bicarbonate. The dried organic phase is concentrated in vacuo and the residue is recrystallized from cyclohexane. 53 g (90%) of 1-difluoromethoxy-2-methoxy-5-nitrobenzene (m.p. 45°–49° C.) are obtained. This is hydrogenated and acetylated analogously to Example 21(a). N-(3-Difluoromethoxy-4-methoxyphenyl)acetamide (m.p. 129°–130° C.) is obtained in 90% yield.

(c) 46 g of the above compound are nitrated with 33 ml of 100% strength nitric acid in dichloromethane analogously to the above instructions. N-(5-Difluoromethoxy-4-methoxy-2-nitrophenyl)acetamide (m.p. 116°–117° C.) is obtained in 99% yield.

(d) 54 g of the above compound are stirred in 810 ml of methanol with 44.8 ml of 30% strength methanolic sodium methylate solution at room temperature for 1 hour. The mixture is concentrated in vacuo and ice-water and glacial acetic acid are added to pH 8 to give 5-difluoromethoxy-4-methoxy-2-nitroaniline (m.p. 144°–145° C.) in 99% yield.

(e) 25 g of the above compound are hydrogenated in 300 ml of methanol over 1.25 g of 10% strength palladium-on-charcoal in accordance with Example 21(d). 26 g (88%) of 3-difluoromethoxy-4-methoxy-1,2-phenylenediamine dihydrochloride of m.p. 218°–220° C. (decomposition) are obtained.

(f) 25 g of the above compound are reacted with 19 g of potassium O-ethyldithiocarbonate in accordance with Example 21(e). 20 g (89%) of the title compound of m.p. 280°–282° C. (decomposition; from isopropanol) are obtained.

28. 5-Difluoromethoxy-6-fluoro-2-mercapto-1H-benzimidazole (a) 1-Difluoromethoxy-2-fluorobenzene (b.p. 76° C./10 kPa $n^{20}/D=1.4340$) is obtained analogously to Example 27a from 2-fluorophenol and chlorodifluoromethane.

(b) 38.4 ml of 100% strength nitric acid are added dropwise to 30 g of the above compound in 300 ml of dichloromethane at $-10°$ C. and the mixture is stirred at $-10°$ C. for 1 hour and at 0° C. for 2.5 hours. Ice-water is added and the mixture is rendered neutral and chromatographed over silica gel with ethyl acetate/cyclohexane (4:1). 34 g of an oil are obtained, which contains about 90% of 1-difluoromethoxy-2-fluoro-4-nitrobenzene and 10% of 1-difluoromethoxy-2-fluoro-5-nitrobenzene (NMR spectrum).

(c) 30 g of the above mixture are hydrogenated and acetylated analogously to Example 21a. Recrystallization from toluene gives 21 g (65%) of N-(4-difluoromethoxy-3-fluorophenyl)acetamide of m.p. 112°–113° C.

(d) 22.5 ml of 100% strength nitric acid are added dropwise to 20 g of the above compound in 200 ml of dichloromethane at 20° C. in the course of 30 minutes and the mixture is subsequently stirred at room temperature for 15 hours. N-(4-difluoromethoxy-5-fluoro-2-nitrophenyl)acetamide of m.p. 72°–74° C. (from cyclohexane) is obtained in 89% yield analogously to Example 27c. Stirring with 1M hydrochloric acid in methanol at 60° C. for several hours gives 4-difluoromethoxy-5-fluoro-2-nitroaniline of m.p. 95°–97.5° C. in 95% yield and, analogously to Example 27(e), 4-difluoromethoxy-5-fluoro-1,2-phenylene-diamine dihydrochloride in 85% yield. Decomposition from 210° C.

(e) 15 g of the above compound are reacted with 11.8 g of potassium O-ethyldithiocarbonate in accordance with Example 21e. 11.1 g (84%) of the title compound of m.p. 275°–276° C. (decomposition, from isopropanol) are obtained.

29. 2,2-Difluoro-5H-[1,3]-dioxolo[4,5-f]benzimidazole-6-thiol (a) 30 g of 4-amino-2,2-difluoro-5-nitro-1,3-benzodioxole in 300 ml of methanol are hydrogenated over 0.5 g of 10% strength palladium-on-charcoal in a circulatory hydrogenation apparatus under atmospheric pressure at room temperature, 2.5 equivalents of methanolic hydrogen chloride solution are added, the mixture is filtered, the solution is concentrated in vacuo and isopropanol and ether are added to the residue to give 35 g (97%) of 2,2-difluoro-1,3-benzodioxole-4,5-diamine dihydrochloride of m.p. 232°–233° C. (decomposition).

(b) 24 g of potassium O-ethyldithiocarbonate (recrystallized from isopropanol) and 9.2 of sodium hydroxide in 55 ml of water are added to 30 g of the above compound in 300 ml of ethanol and the mixture is heated to the boiling point under reflux for 15 hours. The mixture is poured onto 1.5 l of water, brought to pH 14 with sodium hydroxide solution, clarified with active characoal and precipitated with concentrated hydrochloric acid under the influence of heat. The precipitate is filtered off with suction in the cold. 24 g (91%) of the title compound of m.p. 365°–370° C. (decomposition) are obtained.

30. 6,6,7-Trifluoro-6,7-dihydro-1H-[1,4]-dioxino[2,3-f]benzimidazole-2-thiol (a) A mixture of 39.5 ml of 69% strength nitric acid and 46 ml of 97% strength sulfuric acid is added dropwise to 50 g of 2,2,3-trifluoro-2,3-dihydro-1,4-benzodioxine at 5° C. in the course of 1 hour. The mixture is stirred at 10° C. for 1 hours, at 20° C. for 1 hour and at 40° C. for 5 minutes, poured onto 200 g of ice and extracted with dichloromethane. The extract is washed with water, dried with magnesium sulfate and distilled in vacuo. 58 g (94%) of a mixture of 2,2,3-trifluoro-2,3-dihydro-6-nitro- (and 7-nitro)-1,4-benzodioxine of b.p. 68.5° C. (0.15 mbar) and $n^{20}/D$ 1.5080 are obtained. A gas chromatogram with a 10 m fused silica column (Chrompack) shows two peaks in the ratio 2:3.

(b) 35 g of the isomer mixture are hydrogenated in 400 ml of ethanol over 3 g of 10% strength palladium-on-charcoal under atmospheric pressure at 20°-30° C. in a circulatory hydrogenation apparatus, the mixture is filtered and the filtrate is concentrated in vacuo. 30.5 g (100%) of a liquid mixture of 6-amino- (and 7-amino-) 2,2,3-trifluoro-2,3-dihydro-1,4-benzodioxine are obtained.

(c) A mixture of 15.3 g of acetic anhydride and 15 ml of glacial acetic acid is added dropwise to 28 g of the above isomer mixture at 20°-30° C., the mixture is stirred at 30° C. for 30 minutes, 1 ml of water is added, the mixture is stirred at 30° C. for 30 minutes and the solvent is distilled off in vacuo. Recrystallization from toluene gives 19 g of a fraction of a mixture of the isomeric acetamino derivatives of m.p. 128°-133° C.

(d) 14 ml of 100% strength nitric acid, dissolved in 60 ml of dichloromethane, are added dropwise to 17 g of the isomer mixture of the acetamino derivatives, suspended in 100 ml of dichloromethane, at −6° to −8° C. and the mixture is stirred at 0° C. for 2 hours and then at room temperature overnight. The mixture is poured onto 110 g of ice and the organic phase is separated off, washed with water and concentrated in vacuo. The residue (19.8 g) is recrystallized from 20 ml of ethanol. 15.5 g of a mixture of 6-acetamino-2,2,3-trifluoro-2,3-dihydro-7-nitro-1,4-benzodioxine and 7-acetamino-2,2,3-trifluoro-2,3-dihydro-6-nitro-1,4-benzodioxine are obtained.

(e) 14.5 g of the above product mixture are suspended in 80 ml of methanol, and 30 ml of 5M sodium hydroxide solution are added dropwise, while warming to 30° C. The mixture is stirred at room temperature for a further 0.5 hour and poured onto 200 g of ice to give 11.7 g of a mixture of 6-amino-2,2,3-trifluoro-2,3-dihydro-7-nitro-1,4-benzodioxine and 7-amino-2,2,3-trifluoro-2,3-dihydro-6-nitro-1,4-benzodioxine. A sample is separated on a silica gel column with cyclohexane/ethyl acetate (4:1) into two pure isomers of melting points, 110.5°-111.5° C. and 120°-121° C., the NMR spectra of which on a 60 MHz instrument in deuterochloroform are virtually identical.

(f) 10.9 g of the above isomer mixture are hydrogenated in 300 ml of methanol at room temperature under atmospheric pressure over 1 g of 10% strength palladium-on-charcoal in the course of 2.5 hours. 30 ml of 4M hydrogen chloride in methanol are added, the mixture is filtered, the filtrate is concentrated in vacuo and the residue is stirred with 100 ml of ether. 12.6 g (98%) of 2,2,3-trifluoro-2,3-dihydro-1,4-benzodioxine-6,7-diamine dihydrochloride (m.p. 250° C.) are obtained.

(g) 20.5 ml of 4M aqueous potassium hydroxide solution are added to 12 g of the above compound and 8.5 g of potassium O-ethyldithiocarbonate (recrystallized from isopropanol) in 120 ml of ethanol and the mixture is heated to the boiling point under reflux for 17 hours. The mixture is poured onto 300 g of ice, brought to pH 12-13 with potassium hydroxide solution, clarified with active charcoal and precipitated with concentrated hydrochloric acid. Renewed precipitation with acid from alkaline aqueous-alcoholic solution gives 10 g (93%) of the title compound of m.p. 309°-310° C. (decomposition).

31. 6-Chloro-6,7,7-trifluoro-6,7-dihydro-1H-[1,4]dioxino[2,3-f]benzimidazole-2-thiol (a) A mixture of 18.3 ml of 65% strength nitric acid and 15.4 ml of 97% strength sulfuric acid is added dropwise to 18 g of 2-chloro-2,3,3-trifluoro-2,3-dihydro-1,4-benzodioxine at 5° C. and the mixture is stirred at 5°-10° C. for 2 hours and poured onto ice. It is extracted with methylene chloride to give 21.3 g of a mixture of 2-chloro-2,3,3-trifluoro-2,3-dihydro-6-nitro-(and 7-nitro)-1,4-benzodioxine as an oil.

(b) An oily mixture of 2-chloro-2,3,3-trifluoro-2,3-dihydro-1,4-benzodioxine-6- (and 7-)amine is obtained therefrom in 97% yield analogously to Example 30b, and is reacted quantitatively to give a mixture of the corresponding acetamino derivatives in accordance with Example 30c.

(c) 19 g of the above mixture are stirred in 190 ml of dichloromethane with 16 ml of 100% strength nitric acid and the reaction product is purified by chromatography on silica gel by means of cyclohexane/ethyl acetate (4:1). 15 g of a mixture of 6-acetamino-2-chloro-2,3,3-trifluoro-6,7-dihydro-7-nitro-1,4-benzodioxine and 7-acetamino-2-chloro-2,3,3-trifluoro-6,7-dihydro-6-nitro-1,4-benzodioxine are obtained as a pale yellow oil.

(d) 10.2 ml of a 30% strength solution of sodium methylate in methanol are added dropwise to 14.5 g of the above mixture in 100 ml of methanol at 5° C., the mixture is stirred for 1.5 hours without cooling, poured onto ice, neutralized with dilute hydrochloric acid and extracted with dichloromethane and the extract is concentrated in vacuo. 12.7 g of a mixture of 6-amino-2-chloro-2,3,3-trifluoro-2,3-dihydro-7-nitro-1,4-benzodioxine and 7-amino-2-chloro-2,3,3-trifluoro-2,3-dihydro-6-nitro-1,4-benzodioxine are obtained as an orange-colored oil.

(e) 12.4 g of the above mixture are hydrogenated analogously to Example 30f. 12.6 g (99%) of 2-chloro-2,3,3-trifluoro-2,3-dihydro-1,4-benzodioxine-6,7-diamine dihydrochloride are obtained.

(f) 12.4 g of the above compound are reacted with 9.1 g of potassium O-ethyldithiocarbonate and potassium hydroxide solution in ethanol analogously to Example 30g. 9.6 g (74%) of the title compound of m.p. 288°-290° C. (decomposition) are obtained.

32. 2-Chloromethyl-4,5-dimethoxy-pyridinium chloride (a) Chloromethyl-4,5-dimethoxy-pyridinium chloride 3 ml of thionyl chloride, dissolved in 10 ml of methylene chloride, are added dropwise to a solution, cooled to 0° C., of 5 g of 2-hydroxymethyl-4,5-dimethoxypyridine in 40 ml of methylene chloride in the course of one hour, the reaction mixture is then stirred at 20° C. for 4 hours, during which it becomes red-colored, 5 ml of toluene are added and the mixture is concentrated completely on a rotary evaporator (30° C./5 mbar). The oily residue is dissolved in 50 ml of warm isopropanol and the solution is clarified with a little Tonsil ®, filtered and concentration again. The residue is taken up in 10 ml of toluene and the solution is made to crystallize with petroleum ether. After cooling in an ice-bath, the precipitate is filtered off with suction, washed with petroleum ether and dried. 4.6 g (70% of theory) of the title compound 2-chloromethyl-4,5-dimethoxy-pyridinium chloride are obtained as a colorless solid; decomp. at 160°-161° C.

(b) 2-Hydroxymethyl-4,5-dimethoxy-pyridine 19 g of 4,5-dimethoxy-2-methylpyridine 1-oxide are metered into 60 ml of acetic anhydride, warmed to 80°

C., in the course of 30 minutes in a manner such that the temperature does not rise above 100° C. After a further 45 minutes at 85° C., excess acetic anhydride is distilled off in vacuo and the oily dark residue, which essentially consists of the intermediate 2-acetoxymethyl-4,5-dimethoxypyridine is stirred with 80 ml of 2N sodium hydroxide solution at 80° C. for 1 hour. After dilution with 80 ml of water and cooling, the mixture is extracted eight times with 100 ml of methylene chloride each time, the combined organic phases are washed twice with 1N sodium hydroxide solution, dried and concentrated and the crystalline, brownish residue is recrystallized from toluene. 14 g (74% of theory) of 2-hydroxymethyl-4,5-dimethoxy-pyridine of m.p. 122°–124° C. are obtained.

(c) 4,5-Dimethoxy-2-methylpyridine 1-oxide 20 ml of a 30% strength sodium methylate solution are added dropwise to a suspension of 16.9 g of 5-methoxy-2-methyl-4-nitropyridine 1-oxide in 170 ml of dry methanol and the mixture is stirred at 20° C. for 15 hours and then at 50° C. for 4 hours. The pH is brought to 7 by careful addition of concentrated sulfuric acid, while cooling with ice, the mixture is concentrated, the residue is extracted by stirring with 200 ml of methylene chloride, the insoluble constituents are filtered off, 10 ml of toluene are added and the mixture is concentrated to dryness again. 15.2 g (98% of theory) of 4,5-dimethoxy-2-methylpyridine-1-oxide are obtained as colorless crystals of m.p. 118°–121° C.

(d) 5-Methoxy-2-methyl-4-nitropyridine-1-oxide 21.2 g of 5-methoxy-2-methylpyridine 1-oxide are metered into 35 ml of 65% strength nitric acid and warmed to 60° C. in a manner such that the temperature of the reaction mixture does not rise above 80° C. The mixture is stirred at 80° C. for 1 hour, a further 13 ml of 100% strength nitric acid are added to bring the reaction to completion and the mixture is stirred at 60°–70° C. for a further 2 hours. For working up, the mixture is poured onto 300 g of ice. The yellow precipitate which separates out is filtered off over a suction filter, washed with water and dried. The dry solid is boiled up with 200 ml of methylene chloride, filtered off and dried. Further TLC-pure product is isolated by concentration of the filtrate. 22.3 g (87% of theory) of 5-methoxy-2-methyl-4-nitropyridine 1oxide of m.p. 201°–202° C. are obtained as yellow crystals.

(e) 5-Methoxy-2-methylpyridine-1-oxide 120 g of 30% strength hydrogen peroxide solution are added dropwise to a solution of 60.9 g of 5-methoxy-2-methylpyridine in 300 ml of glacial acetic acid at 60° C. in the course of 1 hour and the mixture is subsequently stirred for 3 hours. After destruction of excess per-compounds by addition of active manganese dioxide, the mixture is filtered, the filtrate is concentrated, the residue is clarified hot in 500 ml of ethyl acetate, the mixture is concentrated again and the residue is distilled under 0.3 mbar. 54 g (77% of theory) of 5-methoxy-2-methylpyridine 1-oxide are obtained as a rapidly solidifying oil (b.p. 130° C.); m.p. 80°–84° C.

(f) 5-Methoxy-2-methylpyridine 150 ml of 3-hydroxy-6-methylpyridine are metered into a solution of 84 g of potassium hydroxide in 400 ml of methanol and 500 ml of dimethyl sulfoxide in the course of one hour. After removal of the methanol on a rotary evaporator, 213 g of methyl iodide, dissolved in 100 ml of dimethyl sulfoxide, are added dropwise, while cooling with ice, and the reaction mixture is stirred at 20° C. for 15 hours and subjected to steam distillation. The distillate is extracted continuously in the extractor with methylene chloride and the extract is concentrated. 85 g (56% of theory) of 5-methoxy-2-methylpyridine are obtained as a colorless oil.

33. 2-Chloromethyl-4,5-dimethoxy-3-methylpyridinium chloride (a) 2-Chloromethyl-4,5-dimethoxy-3-methylpyridinium chloride.

3.45 g (99% of theory) of the title compound are obtained as colorless crystals by the procedure described in Example 32a by reacting 2.7 g of 2-hydroxymethyl-4,5-dimethoxy-3-methylpyridine with 4 g of thionyl chloride in 25 ml of methylene chloride, after a reaction time of 1 hour and after a simplified method of working up characterized by addition of 10 ml of toluene, removal of the methylene chloride and excess thionyl chloride by distillation, removal of the crystals precipitated by filtration with suction and drying; decomp. at 125°–126° C.

(b) 2-Hydroxymethyl-4,5-dimethoxy-3-methylpyridine 4.5 g of 4,5-dimethoxy-2,3-dimethylpyridine 1-oxide are warmed to 110° C. in 20 ml of acetic anhydride in the course of 30 minutes and the mixture is then concentrated on a rotary evaporator. The oily residue, which consists of the intermediate 2-acetoxymethyl-4,5-dimethoxy-3-methylpyridine, is stirred in 30 ml of 3N sodium hydroxide solution at 80° C. for 2 hours, the mixture is extracted, after cooling, five times with 30 ml of methylene chloride each time, the combined organic phases are washed twice with 2N sodium hydroxide solution, dried and concentrated and the residue is stirred with petroleum ether, filtered off with suction and dried. 4.0 g (89% of theory) of 2-hydroxymethyl-4,5-dimethoxy-3-methylpyridine of m.p. 91°–92° C. are obtained.

(c) 4,5-Dimethoxy-2,3-dimethylpyridine 1-oxide 6.3 g of 4,5-dimethoxy-2,3-dimethylpyridine are dissolved in 120 ml of methylene chloride, 20 g of m-chloroperoxybenzoic acid are added successively and the mixture is stirred first at 20° C. for 2 hours and then at 40° C. for 4 hours. After addition of 20 ml of 5N sodium hydroxide solution, the mixture is washed three times with a mixture of 5% strength sodium thiosulfate solution and 5% strength sodium carbonate solution, the aqueous phase is back-extracted twice with methylene chloride and the combined organic phases are dried over magnesium sulfate and concentrated. 4.6 g (66% of theory) of 4,5-dimethoxy-2,3-dimethylpyridine 1-oxide are obtained. The Rf value in methylene chloride/methanol 19:1 is 0.25.

(d) 4,5-Dimethoxy-2,3-dimethylpyridine 7.4 g (74% of theory) of 4,5-dimethoxy-2,3-dimethylpyridine are obtained as a colorless, gradually crystallizing oil of m.p. 36°–38° C. by the procedure described in Example 32f by reaction of 9.18 g of 5-hydroxy-4-methoxy-2,3-dimethylpyridine in 50 ml of dimethyl sulfoxide first with 3.6 g of sodium hydroxide and then with 8.95 g of methyl iodide.

(e) 5-Hydroxy-4-methoxy-2,3-dimethylpyridine 1,000 g of 4-methoxy-2,3dimethylpyridine 1-oxide are metered into 3 l of acetic anhydride at 100° C. in the course of 7 hours while stirring, and the mixture is subsequently stirred at 100° C. for a further 3 hours. The mixture is allowed to cool and is concentrated completely at 70° C./10 mbar and the residue is then distilled under $10^{-2}$ mbar. The fraction with a boiling range from 95° to 145° C. (mixture of the intermediate 5-acetoxy-4-methoxy-2,3-dimethylpyridine and 2- acetoxymethyl-4-methoxy-3-methylpyridine) is removed (952 g) and added to 3.5 l of 2N sodium hydroxide solution, warmed to 50° C., in the course of 30 minutes.

The mixture is stirred at 50° C. until a clear solution is formed (about 3 hours), is allowed to cool and is extracted three times with 1 l of methylene chloride each time. The combined organic phases are back-extracted twice with 0.5 l of 1N sodium hydroxide solution each time and the combined aqueous phases are then brought to pH 7.5 with half-concentrated hydrochloric acid, with stirring. The solid which has precipitated out is filtered off, rinsed and dried to constant weight. 5-Hydroxy-4-methoxy-2,3-dimethylpyridine of m.p. 274°–276° C. is obtained.

34. 2-Chloromethyl-3,4-dimethoxy-pyridinium chloride (a) 2-Chloromethyl-3,4-dimethoxy-pyridinium chloride 4.2 g (93% of theory) of the title compound are obtained as a colorless solid of m.p. 151°–152° C. (decomp.) by the procedure described in Example 32a by reacting 3.38 g of 2-hydroxymethyl-3,4-dimethoxypyridine with 2 ml of thionyl chloride in 30 ml of methylene chloride, after a reaction time of 2.5 hours and after the type of working up described in Example 33a.

(b) 2-Hydroxymethyl-3,4-dimethoxypyridine

After adding 15 ml of 2N sodium hydroxide solution, 4.8 g of 2-acetoxymethyl-3,4-dimethoxypyridine are stirred vigorously at 80° C., whereupon a homogeneous solution forms from the initial two-phase mixture. After 2 hours, the solution is allowed to cool and is extracted five times with 30 ml of methylene chloride each time, the combined organic phases are washed twice with 5 ml of 0.3N sodium hydroxide solution each time, dried over potassium carbonate, filtered and concentrated and the distillation residue is stirred with petroleum ether. 3.6 g (96% of theory) of 2-hydroxymethyl-3,4-dimethoxy-pyridine are obtained as a colorless solid of m.p. 87°–89° C.

(c) 2-Acetoxymethyl-3,4-dimethoxypyridine 4.8 g (28 mmol) of 3,4-dimethoxy-2-methylpyridine 1-oxide are metered into 25 ml of acetic anhydride at 85° C. in the course of one hour, the mixture is stirred at the same temperature for one hour and concentrated completely in vacuo. The brown oily residue is distilled in a bulb tube still under 1 Pa. 5.3 g (90% of theory) of 2-acetoxymethyl-3,4-dimethoxypyridine are obtained; b.p. 125°–130° C.

(d) 3,4-Dimethoxy-2-methylpyridine 1-oxide 4.5 g (25 mmol) of 3-methoxy-2-methyl-4-nitropyridine 1-oxide are stirred at 40° C. in 75 ml of dry methanol, after addition of 4.7 ml of 30% strength sodium methylate solution, for 16 hours. The mixture is then cooled, brought to pH 7 with concentrated sulfuric acid, filtered and concentrated completely in vacuo, the oily, reddish residue is taken up in 50 ml of toluene, the mixture is filtered again to remove insoluble constituents and the filtrate is concentrated to dryness. The yellow oily residue crystallizes on an ice-bath and is finally extracted by stirring with 30 ml of petroleum ether (50/70) at 40° C. filtration and drying in a desiccator gives 5.2 g (88% of theory) of 3,4-dimethoxy-2-methyl-pyridine 1-oxide in the form of pale yellow crystals of m.p. 111°–113° C.

(e) 3-Methoxy-2-methyl-4-nitropyridine 1-oxide 8 ml of concentrated nitric acid are added in four portions of 2 ml each to 5.4 g of 3-methoxy-2-methyl-pyridine 1-oxide in 12 ml of glacial acetic acid at 80° C. in the course of 6 hours, the mixture is stirred at the same temperature overnight, a further 8 ml of nitric acid are added in three portions in the course of 6 hours and the mixture is stirred for a further 15 hours. After cooling, the mixture is poured onto ice (40 g) and brought to pH 6 with 10N sodium hydroxide solution, the by-product (3-methoxy-2-methyl-4-nitropyridine) which has precipitated out is filtered off and the filtrate is extracted four times with 50 ml of methylene chloride. After drying, the combined organic phases are concentrated completely and the residue is recrystallized from a little methylene chloride/petroleum ether. 4.2 g (57% of theory) of the title compound are obtained in the form of yellow crystals of m.p. 103°–104° C.

(f) 3-Methoxy-2-methylpyridine 1-oxide 15.3 g (0.124 mole) of 3-methoxy-2-methylpyridine are dissolved in 100 ml of glacial acetic acid, and 40 ml of 30% strength hydrogen peroxide are added in 4 portions at 80° C. in the course of 6 hours. The mixture is stirred for a further three hours and then concentrated in vacuo (1.5 kPa), and two 50 ml portions of acetic acid are added, the mixture being concentrated completely after each addition. Following negative detection of per-compounds, the mixture is distilled in a bulb tube oven. The fraction which distills at 120° C. (1.5 Pa) is extracted by stirring in a little diethyl ether and the solid is filtered off and dried. 12 g (60% of theory) of 3-methoxy-2-methylpyridine 1-oxide are obtained in the form of colorless crystals of m.p. 72°–78° C.

(g) 3-Methoxy-2-methylpyridine 15.5 g (90% of theory) of 3-methoxy-2-methylpyridine are obtained as a colorless oil by the procedure described in Example 32f by reaction of 13.7 g (125 mmol) of 3-hydroxy-2-methylpyridine with 9.2 ml of methyl iodide, with the addition of 46 ml of 3M methanolic potassium hydroxide solution and after a reaction time of 3 hours.

COMMERCIAL APPLICABILITY

The dialkoxypyridines of formula I and their pharmacologically-acceptable salts have useful pharmacological properties which render them commercially useful. In particular, they inhibit gastric acid secretion in warm-blooded animals. In addition, they exhibit an excellent protective action on the stomach and intestines of warm-blooded animals. This protective action on the stomach and intestine is observed even upon administering doses below those necessary to inhibit acid secretion. The compounds according to the invention are distinguished by the absence of substantial side effects and by a wide therapeutic range.

The term "protection of the stomach and intestine" comprises the prevention and treatment of gastrointestinal diseases, primarily those which are non-cancerous in origin, especially gastrointestinal inflammatory diseases and lesions (such as, for example, gastric ulcer, duodenal ulcer, gastritis and stomach irritation caused by hyperacidity or medicaments), which can be caused, for example, by microorganisms, bacterial toxins, medicaments (for example certain anti-inflammatories and anti-rheumatics), other chemicals (for example ethanol), gastric acid or stress situations.

Another advantage of the compounds according to the invention is their comparatively high chemical stability.

Surprisingly, the compounds according to the invention are clearly superior (in their excellent properties) to prior art compounds. On the basis of these properties, the dialkoxypyridines and their pharmacologically-acceptable salts are outstandingly suitable for use in human and veterinary medicine, where they are used, in particular, for the treatment and prophylaxis of diseases of the stomach and intestine and those conditions which result from excessive secretion of gastric juice.

The invention thus also relates to a method for treating mammals suffering from the noted illnesses. The method comprises the administration of a therapeutically and pharmacologically-appropriate amount of one or more of the specified dialkoxypyridines to the sick mammal.

The invention furthermore relates to the compounds according to the invention which are used in this method. The invention moreover relates to the use of the present compounds in the production of medicaments.

The invention also relates to medicaments which contain one or more dialkoxypyridines of formula I and/or their pharmacologically-acceptable salts.

The medicaments are prepared by conventional processes. As medicaments, the pharmacologically-active compounds (=active compounds) according to the invention are used either as such or, preferably, in combination with suitable pharmaceutical auxiliaries, in the form of tablets, coated tablets, capsules, suppositories, plasters (for example as TTS), emulsions, suspensions or solutions, the content of active compound advantageously being between 0.1 and 95%, by weight.

The auxiliaries which are suitable for the desired medicament formulations are known. Solvents, gelling agents, suppository bases, tablets, auxiliaries and other active compound vehicles, as well as antioxidants, dispersing agents, emulsifiers, antifoaming agents, flavor correctants, preservatives, solubilizing agents, colorants or, in particular, permeation promoters and complexing agents (for example cyclodextrins) are useful.

The active compounds are administered orally, parenterally or percutaneously.

In general, it is advantageous in human medicine to administer the active compound or compounds, in the case of oral administration, in a daily dose of from about 0.01 to about 20, preferably 0.05 to 5 and, in particular, 0.1 to 1.5 mg/kg of body weight, if appropriate in the form of several, preferably 1 to 4, individual doses, to achieve the desired result. In the case of parenteral treatment, similar or (especiallly in the case of intravenous administration of the active compound) as a rule lower dosages are effective. The particular optimum dosage and mode of administration of the active compounds required are easily determined by those skilled in the art.

When a compound (and/or a salt thereof) according to the invention is used for treatment of the noted conditions, the pharmaceutical formulation optionally contains one or more pharmacologically-active constituents from other groups of medicaments, such as antacids, for example aluminum hydroxide or magnesium aluminate; tranquilizers, such as benzodiazepines, for example diazepam; spasmolytics, such as bietamiverine and camylofin; anticholinergics, such as oxyphencyclimine and phencarbamide; local anesthetics, such as tetracaine and procaine; and, if appropriate, also enzymes, vitamins or amino acids.

Combination of the compounds according to the invention with other drugs which inhibit acid secretion, such as $H_2$-blockers (for example cimetidine and ranitidine), and furthermore with so-called peripheral anticholinergics (for example pirenzepine, telenzepine and zolenzepine) and with gastrin antagonists, with the aim of intensifying the main action in the additive or super-additive sense and/or eliminating or reducing side effects, is to be particularly emphasized.

PHARMACOLOGY

The excellent protective action on the stomach and the gastric secretion inhibition shown by the compounds according to the invention is demonstrated in tests using the Shay rat model. The compounds according to the invention investigated appear in the following table:

| Serial No. | Name of the compound |
|---|---|
| 1 | 2-[(4,5-dimethoxy-2-pyridyl)methylsulfinyl]-5-trifluoromethoxy-1H—benzimidazole |
| 2 | 2-[(4,5-dimethoxy-3-methyl-2-pyridyl)methylsulfinyl]-5-trifluoromethoxy-1H—benzimidazole |
| 3 | 2-[(4,5-dimethoxy-2-pyridyl)methylsulfinyl]-5-(1,1,2,2-tetrafluoroethoxy)-1H—benzimidazole |
| 4 | 2,2-difluoro-6-[(4,5-dimethoxy-2-pyridyl)methylthio]-5H—[1,3]-dioxolo[4,5-f]benzimidazole |
| 5 | 2,2-difluoro-6-[(4,5-dimethoxy-2-pyridyl)methylsulfinyl]-5H—[1,3]-dioxolo[4,5-f]-benzimidazole |

The influence of the compounds investigated on the formation of gastric lesions triggered by pylorus ligature (4 hours; Shay rat) and oral administration of 100 mg/kg of acetylsalicylic acid on the inhibition of gastric secretion (HCl) in rats during 4 hours is shown in the following table:

| | Protective Action on the Stomach and Inhibition of Gastric Secretion | | | |
|---|---|---|---|---|
| Serial No. | n [Number of animals] | Protective action on the stomach (rat) inhibition of the lesion index ED50+) [mg/kg, p.o.] | Inhibition of the HCl secretion in the stomach (rat; total of 4 hours) | |
| | | | % inhibition of HCl secretion (++) | ED25+   ED50+ [mg/kg, p.o.] |
| 1 | 40 | 0.6 | 15 | 1.0   ~3 |
| 2 | 48 | 0.8 | 25 | 0.7   1.7 |
| 3 | 56 | 0.6 | 18 | ~1    3.4 |
| 4 | 40 | 3.5 | 28 | 3.0   6.5 |
| 5 | 72 | ~1  | 25 | 1.0   3.0 |

ED25+ and ED50+ = dose which reduces the lesion index and the HCL secretion (over 4 hours) in the rat stomach by 25% and 50% in the treated group in comparison with the control group.
(++) = after administration of the antiulcerous ED50

The antiulcerogenic action was tested in Shay rats:

Ulcers were provoked in rats which had fasted for 24 hours (female, 180–200 g, 4 animals per cage on a high grid) by pylorus ligature (under diethyl ether anesthesia) and oral administration of 100 mg/10 ml/kg of acetylsalicylic acid. The substances to be tested are administered orally (10 ml/kg) one hour before the pylorus ligature. The wound is closed by means of Michel clamps. 4 hours thereafter, the animals are sacrificed under ether anesthesia by atlas dislocation and the stomach is resected. The stomach is opened longitudinally and fixed to a cork plate, after first determining the amount of secreted gastric juice (volume) and later its HCl content (titration with sodium hydroxide solution). The number and size (=diameter) of ulcers present are determined with a stereomicroscope with 10- fold magnification. The product of the degree of severity (according to the following points scale) and number of ulcers serves as the individual lesion index.

| Point scale: | | |
|---|---|---|
| no ulcers | | 0 |
| ulcer diameter | 0.1-1.4 mm | 1 |
| | 1.5-2.4 mm | 2 |
| | 2.5-3.4 mm | 3 |
| | 3.5-4.4 mm | 4 |
| | 4.5-5.4 mm | 5 |
| | >5.5 mm | 6 |

The reduction in the average lesion index of each treated group compared with that of the control group (=100%) serves as a measure of the antiulcerogenic effect. The ED25 and ED50 designate the doses which reduce the average lesion index and the HCL secretion by 25% and 50%.

TOXICITY

The LD50 of all tested compounds is greater than 1,000 mg/kg [p.o] in mice.

What is claimed is:

1. A dialkoxypyridine of formula I

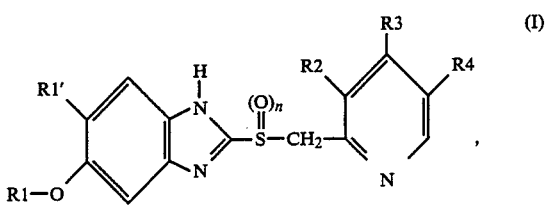

wherein
$R_1$ is 1-3C-alkyl which is completely or predominantly substituted by fluorine, or chlorodifluoromethyl;
$R_1'$ is a hydrogen atom, halo, trifluoromethyl, 1-3C-alkyl, or 1-3C-alkoxy which is unsubstituted or completely or predominatly substituted by fluorine; or
$R_1$ and $R_1'$, together with the oxygen atom to which $R_1$ is bonded, is 1-2C-alkylenedioxy which is optionally completely or partly substituted by fluorine, or chlorotrifluoroethylenedioxy;
$R_3$ is 1-3C-alkoxy;
one of $R_2$ and $R_4$ is 1-3C-alkoxy and the other is a hydrogen atom or 1-3C-alkyl; and
n is 0 or 1;
or a salt thereof.

2. A compound according to claim 1 wherein
$R_1$ is 1-3C-alkyl which is completely or predominantly substituted by fluorine, or chlorodifluoromethyl;
$R_1'$ is a hydrogen atom, halo, trifluoromethyl, 1-3C-alkyl, or 1-3C-alkoxy which is unsubstituted or completely or predominantly substituted by fluorine;
$R_3$ is 1-3C-alkoxy;
one of $R_2$ and $R_4$ is 1-3C-alkoxy and the other is a hydrogen atom or 1-3C-alkyl; and
n is 0 or 1, or a salt thereof.

3. A compound according to claim 1 wherein,
$R_1$ and $R_1'$, together with the oxygen atom to which $R_1$ is bonded, is 1-2C-alkylenedioxy which is unsubstituted or completely or partly substituted by fluorine, or chlorotrifluoroethylenedioxy,
$R_3$ is 1-3C-alkoxy;
one of $R_2$ and $R_4$ is 1-3C-alkoxy and the other is a hydrogen atom or a 1-3C-alkyl radical and n is 0 or 1, or a salt thereof.

4. A compound according to claim 2, wherein $R_1'$ is a hydrogen atom and $R_1$, $R_2$, $R_3$, and $R_4$ and n have their previously-ascribed meanings, or a salt thereof.

5. A compound according to claim 2 wherein $R_1$ is 1,1,2,2-tetrafluoroethyl, trifluoromethyl, 2,2,2-trifluoroethyl, difluoromethyl or chlorodifluoromethyl, $R_1'$ is a hydrogen atom, $R_3$ is methoxy, one of $R_2$ and $R_4$ is methoxy and the other is a hydrogen atom or methyl and n is 0 or 1, or a salt thereof.

6. A compound according to claim 2, wherein $R_1$ is 1,1,2,2-tetrafluoroethyl, trifluoromethyl, 2,2,2-trifluoroethyl or difluoromethyl, $R_1'$ is a hydrogen atom, $R_3$ is methoxy, one of $R_2$ and $R_4$ is methoxy and the other is a hydrogen atom or methyl and n is 0 or 1, or a salt thereof.

7. A compound according to claim 4, 5, or 6, wherein $R_2$ is a hydrogen atom or methyl and $R_3$ and $R_4$ are methoxy, or a salt thereof.

8. A compound according to claim 4, 5 or 6, wherein $R_4$ is a hydrogen atom and $R_2$ and $R_3$ are methoxy, or a salt thereof.

9. A compound according to claim 3, wherein $R_1$ and $R_1'$, together with the oxygen atom to which $R_1$ is bonded, are 1-2C-alkylenedioxy, and $R_2$, $R_3$, $R_4$ and n have the meanings given in claim 3, or a salt thereof.

10. A compound according to claim 3, wherein $R_1$ and $R_1'$, together with the oxygen atom to which $R_1$ is bonded, are methylenedioxy or ethylenedioxy, and $R_2$, $R_3$, $R_4$ and n have the meanings given in claim 3, or a salt thereof.

11. A compound according to claim 3, wherein $R_1$ and $R_1'$, together with the oxygen atom to which $R_1$ is bonded, are 1-2C-alkylenedioxy which is completely or partly substituted by fluorine and $R_2$, $R_3$, $R_4$ and n have the meanings given in claim 3, or a salt thereof.

12. A compound according to claim 3, wherein $R_1$ and $R_1'$, together with the oxygen atom to which $R_1$ is bonded, are difluoromethylenedioxy or 1,1,2-trifluoroethylenedioxy and $R_2$, $R_3$, $R_4$ and n have the meanings given in claim 3, or a salt thereof.

13. A compound according to claim 3 wherein $R_1$ and $R_1'$, together with the oxygen atom to which $R_1$ is bonded, are difluoromethylenedioxy or methylenedioxy and $R_2$, $R_3$, $R_4$ and n have the meanings given in claim 3, or a salt thereof.

14. A compound according to claims 9, 10, 11, 12 or 13, wherein $R_2$ is a hydrogen atom or methyl, $R_3$ is methoxy, $R_4$ is methoxy, or a salt thereof.

15. A compound according to claims 9, 10, 11, 12 or 13, wherein $R_2$ is methoxy, $R_3$ is methoxy, and $R_4$ is a hydrogen atom or methyl, or a salt thereof.

16. A compound according to claims 9, 10, 11, 12, or 13, wherein $R_2$ is methoxy, $R_3$ is methoxy and $R_4$ is methyl, or a salt thereof.

17. A compound according to claim 1, wherein n is 0, or an acid addition salt thereof.

18. A compound according to claim 1, wherein n is 1, or a salt thereof with a base.

19. A compound according to claim 1 selected from the group consisting of 2-[(4,5-dimethoxy-2-pyridyl)methylsulfinyl]-5-trifluoromethoxy-1H-benzimidazole, 2-[(4,5-dimethoxy-3-methyl-2-pyridyl)methylsulfinyl]-5-trifluoromethoxy-1H-benzimidazole, 2-[(4,5-dimethoxy-2-pyridyl)methylsulfinyl]-5-(1,1,2,2-tetrafluoroethoxy)-1H-benzimidazole, 2,2-difluoro-6-[(4,5-dimethoxy-2-pyridyl)methylthio]-5H-[1,3]-dioxolo[4,5-f]benzimidazole and 2,2-difluoro-6-[(4,5-dimethoxy-2- pyridyl)methylsulfinyl]-5H-[1,3]-dioxolo[4,5-f]benzimidazole, or a salt thereof.

20. A pharmaceutically-acceptable compound which is a dialkoxypyridine according to claim 1 or a salt thereof.

21. A compound according to claim 1 which is 2-[(3,4-dimethoxy-2-pyridyl)methylsulfinyl]-5-(1,1,2,2-tetrafluoroethoxy)-1H-benzimidazole or a pharmacologically-compatible salt thereof.

22. A compound according to claim 1 which is 5-difluoromethoxy-2-[(3,4-dimethoxy-2-pyridyl)methylsulfinyl]-1H-benzimidazole or a pharmacologically-compatible salt thereof.

23. A compound according to claim 1 wherein R1 is difluoromethyl, 1,1,2,2-tetrafluoroethyl or 2,2,2-trifluoroethyl; R1' is a hydrogen atom or methoxy; or R1 and R1', together with the oxygen atom to which R1 is bound, is difluoromethylenedioxy or 1,1,2-trifluoroethylenedioxy; R3 is methoxy; one of R2 and R4 is methoxy, and the other is hydrogen; and n is 0 or 1; or a salt thereof.

24. A compound according to claim 1 wherein R1 is difluoromethyl, 1,1,2,2-tetrafluoroethyl or 2,2,2-trifluoroethyl; R1' is a hydrogen atom; R3 is methoxy; one of R2 and R4 is methoxy, and the other is hydrogen; and n is 0 or 1; or a salt thereof.

25. The compound according to claim 1 which is 5-difluoromethoxy-2-[(3,4-dimethoxy-2-pyridyl)methylsulfinyl]-1H-benzimidazole sodium salt.

26. A medicament composition useful to inhibit gastric acid secretion in and to protect the stomach and intestines of warm-blooded animals and comprising an active ingredient and a pharmaceutical auxiliary, the active ingredient comprising from 0.1 to 95 percent by weight of at least one pharmaceutically-acceptable compound according to claim 20.

27. A method for treatment or prophylaxis of illness based on excessive secretion of hydrochloric acid by the stomach which comprises administering an effective amount of a compound according to claim 20 to a mammal suffering from said illness.

28. A method for providing protective action for the stomach and intestines which comprises administering an effective amount of a compound according to claim 20 to a mammal.

* * * * *

UNITED STATES PATENT AND TRADEMARK OFFICE
CERTIFICATE OF CORRECTION

PATENT NO. : 4,758,579

DATED : July 19, 1988

INVENTOR(S) : Bernhard KOHL; Ernst STURM; Georg RAINER

It is certified that error appears in the above-identified patent and that said Letters Patent is hereby corrected as shown below:

Column 2, line 58, "1,1,2,2L" should read --1,1,2,2--. Column 3, line 40, "alkylenedioxyradical" should read --alkylenedioxy radical--; line 61, "represent" should read --represents--. Column 8, line 10, "4,5-d" should read --4,5-f--. Column 16, line 67, "Example 'by" should read --Example 1 by--. Column 22, line 47, "hydrochloric" should read --nitric--; line 59, "24" should read --21--. Column 24, line 67, "hours," should read --hour,--. Column 26, line 58, "concentration" should read --concentrated--. Column 27, line 45, "1oxide" should read --1-oxide--. Column 29, line 61, "filtration" should read --Filtration--.

Signed and Sealed this

Fourth Day of July, 1989

Attest:

DONALD J. QUIGG

Attesting Officer

Commissioner of Patents and Trademarks

UNITED STATES PATENT AND TRADEMARK OFFICE

(12)          CERTIFICATE EXTENDING PATENT TERM
UNDER 35 U.S.C. § 156

| | | | |
|---|---|---|---|
| (68) | PATENT NO. | : | 4,758,579 |
| (45) | ISSUED | : | July 19, 1988 |
| (75) | INVENTOR | : | Kohl, et al. |
| (73) | PATENT OWNER | : | Altana Pharma AG |
| (95) | PRODUCT | : | Protonix® (pantoprazole sodium) |

This is to certify that an application under 35 U.S.C. § 156 has been filed in the United States Patent and Trademark Office, requesting extension of the term of U.S. Patent No. 4,758,579 based upon the regulatory review of the product Protonix® (pantoprazole sodium) by the Food and Drug Administration. Since it appears that the requirements of the law have been met, this certificate extends the term of the patent for the period of

(94)                     5 years from July 19, 2005, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 7th day of January 2004

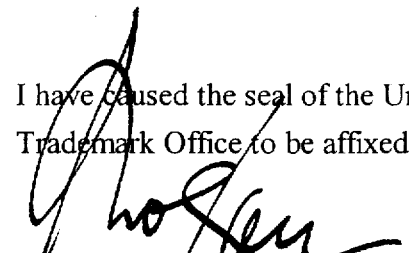

JAMES E. ROGAN
Under Secretary of Commerce for Intellectual Property and
Director of the United States Patent and Trademark Office